(12) United States Patent
MacLaughlin et al.

(10) Patent No.: US 12,725,707 B2
(45) Date of Patent: Sep. 1, 2026

(54) MEDICAL CARE MANAGEMENT SYSTEM AND METHOD

(71) Applicant: DeLorean Artificial Intelligence, Inc., Palm Beach, FL (US)

(72) Inventors: Severence M. MacLaughlin, Palm Beach, FL (US); Ram Prasad Bora, Palm Beach, FL (US); Dhiraj Sharma, Palm Beach, FL (US)

(73) Assignee: DeLorean Artificial Intelligence, Inc., Palm Beach, FL (US)

(*) Notice: Subject to any disclaimer, the term of this patent is extended or adjusted under 35 U.S.C. 154(b) by 112 days.

(21) Appl. No.: 18/482,741

(22) Filed: Oct. 6, 2023

(65) Prior Publication Data

US 2025/0118431 A1 Apr. 10, 2025

(51) Int. Cl.
*G16H 50/20* (2018.01)
*G06N 5/022* (2023.01)
(Continued)

(52) U.S. Cl.
CPC ............. *G16H 50/20* (2018.01); *G06N 5/022* (2013.01); *G16H 20/40* (2018.01); *G16H 50/30* (2018.01); *G16H 50/50* (2018.01)

(58) Field of Classification Search
CPC ........ G16H 50/20; G16H 50/70; G16H 10/60; G16H 50/30; G16H 15/00
See application file for complete search history.

(56) References Cited

U.S. PATENT DOCUMENTS 5,966,126 A 10/1999 Szabo
8,548,937 B2 10/2013 Saigal et al.
(Continued)

FOREIGN PATENT DOCUMENTS

CN 105022740 A 11/2015
CN 106096657 A 11/2016
(Continued)

OTHER PUBLICATIONS

Li, Dan, et al. "Machine learning-aided risk stratification system for the prediction of coronary artery disease." International Journal of Cardiology 326 (2021): 30-34. (Year: 2021).*
(Continued)

*Primary Examiner* — Constantine Siozopoulos
(74) *Attorney, Agent, or Firm* — Pillsbury Winthrop Shaw Pittman LLP

(57) ABSTRACT

Provided are techniques including receiving patient data; generating, based on the patient data, a patient risk stratification including: generating stratification scoring based on the patient data; and determining, based on the stratification scoring, a binary classification; generating, based on the patient data, a patient risk level assignment including: generating risk level scoring based on the stratification scoring and the binary classification; and determining, based on the risk level scoring, a risk category; generating a set of patient next best actions including: determining, based on the patient data, a patient outcome prediction; and generating, based on the predictions of patient outcomes, the set of patient next best actions; generating a patient disease state transition prediction including: determining, based on the patient data, a set of transition probabilities; generating, a patient unknown identification prediction including: determining, based on the patient data, a disease propensity score; and generating a corresponding patient diagnosis report.

15 Claims, 16 Drawing Sheets

(51) Int. Cl.

| | |
|---|---|
| ***G16H 20/40*** | (2018.01) |
| ***G16H 50/30*** | (2018.01) |
| ***G16H 50/50*** | (2018.01) |

(56) References Cited

U.S. PATENT DOCUMENTS

| | | | | |
|---|---|---|---|---|
| 10,483,003 | B1 | 11/2019 | McNair et al. | |
| 11,093,880 | B2 | 8/2021 | Anderson et al. | |
| 11,093,884 | B2 | 8/2021 | Devarakonda et al. | |
| 11,210,300 | B2 | 12/2021 | Ignatyev | |
| 11,282,022 | B2 | 3/2022 | Devarakonda et al. | |
| 11,514,379 | B2 | 11/2022 | Adrian et al. | |
| 11,581,092 | B1 | 2/2023 | McNair et al. | |
| 11,723,560 | B2 | 8/2023 | Constantin et al. | |
| 11,790,412 | B2 | 10/2023 | Pachauri et al. | |
| 2002/0143635 | A1 | 10/2002 | Goodwin, III | |
| 2005/0234761 | A1 | 10/2005 | Pinto | |
| 2006/0085408 | A1 | 4/2006 | Morsa | |
| 2006/0190310 | A1 | 8/2006 | Gudla | |
| 2007/0043609 | A1 | 2/2007 | Imam | |
| 2007/0043611 | A1 | 2/2007 | Newman | |
| 2007/0112704 | A1 | 5/2007 | Tomkins et al. | |
| 2007/0288297 | A1 | 12/2007 | Karras et al. | |
| 2010/0010878 | A1 | 1/2010 | Pinto et al. | |
| 2010/0287059 | A1 | 11/2010 | Mccoy et al. | |
| 2011/0270646 | A1 | 11/2011 | Prasanna et al. | |
| 2011/0295783 | A1 | 12/2011 | Zhao et al. | |
| 2012/0059779 | A1 | 3/2012 | Syed et al. | |
| 2012/0284213 | A1 | 11/2012 | Lin et al. | |
| 2012/0303412 | A1 | 11/2012 | Etzioni et al. | |
| 2013/0151311 | A1 | 6/2013 | Smallwood et al. | |
| 2014/0081738 | A1 | 3/2014 | Abraham | |
| 2014/0101143 | A1 | 4/2014 | Zhang | |
| 2014/0372351 | A1 | 12/2014 | Sun et al. | |
| 2015/0032526 | A1 | 1/2015 | Calman et al. | |
| 2015/0100356 | A1 | 4/2015 | Bessler | |
| 2015/0149237 | A1 | 5/2015 | Brock | |
| 2016/0063506 | A1 | 3/2016 | Hicks | |
| 2016/0239808 | A1 | 8/2016 | Ryu | |
| 2018/0060744 | A1 | 3/2018 | Achin et al. | |
| 2018/0218247 | A1 | 8/2018 | Lee et al. | |
| 2018/0315141 | A1 | 11/2018 | Hunn | |
| 2019/0116265 | A1 | 4/2019 | Avila et al. | |
| 2019/0130425 | A1 | 5/2019 | Lei | |
| 2019/0139054 | A1 | 5/2019 | Mathrubootham et al. | |
| 2019/0259043 | A1 | 8/2019 | Koneri et al. | |
| 2019/0378074 | A1 | 12/2019 | Mcphatter | |
| 2020/0184417 | A1 | 6/2020 | Rosenfeld et al. | |
| 2020/0210922 | A1 | 7/2020 | Devarakonda | |
| 2020/0293946 | A1 | 9/2020 | Sachan et al. | |
| 2021/0014136 | A1 | 1/2021 | Rath | |
| 2021/0049700 | A1 | 2/2021 | Nguyen | |
| 2021/0202103 | A1 | 7/2021 | Bostic et al. | |
| 2021/0310075 | A1 | 10/2021 | Maher et al. | |
| 2021/0343411 | A1 | 11/2021 | Zhang et al. | |
| 2021/0390498 | A1 | 12/2021 | Ohlsson et al. | |
| 2022/0138785 | A1 | 5/2022 | Zarakas et al. | |
| 2022/0172257 | A1 | 6/2022 | Mustafi | |
| 2022/0263731 | A1 | 8/2022 | Gupta et al. | |
| 2022/0358514 | A1 | 11/2022 | Duff | |
| 2023/0119881 | A1 | 4/2023 | Makhija | |
| 2023/0177516 | A1 | 6/2023 | He | |
| 2023/0177537 | A1 | 6/2023 | Maclaughlin | |
| 2023/0267370 | A1 | 8/2023 | Copeland | |
| 2023/0307115 | A1* | 9/2023 | Kumar | G06F 40/30 |
| 2024/0054447 | A1 | 2/2024 | Kwon | |
| 2024/0119346 | A1 | 4/2024 | Chang et al. | |
| 2024/0177841 | A1 | 5/2024 | Mamaghani | |
| 2024/0378494 | A1 | 11/2024 | Biswas | |
| 2024/0386372 | A1 | 11/2024 | Vanbrocklin | |
| 2025/0181592 | A1 | 6/2025 | Khan | |
| 2025/0181602 | A1 | 6/2025 | Khan | |

FOREIGN PATENT DOCUMENTS

| | | | | |
|---|---|---|---|---|
| CN | 107515898 | A | 12/2017 | |
| CN | 108520045 | A | 9/2018 | |
| JP | 2007141036 | A | 6/2007 | |
| KR | 10-2018-0029593 | A | 3/2018 | |
| KR | 10-2020-0099284 | A | 8/2020 | |
| KR | 1020210042709 | A | 4/2021 | |
| WO | 2020-163381 | A1 | 8/2020 | |
| WO | WO-2020245727 | A1 * | 12/2020 | G06N 3/006 |

OTHER PUBLICATIONS

"LightGBM", Wikipedia.org, retrieved Nov. 16, 2023, pp. 1-3.

"Logistic regression", Wikipedia.org, retrieved Nov. 16, 2023, pp. 1-30.

"Long short-term memory", Wikipedia.org, retrieved Nov. 16, 2023, pp. 1-14.

"Machine learning", Wikipedia.org, retrieved Nov. 16, 2023, pp. 1-34.

"Naive Bayes classifier", Wikipedia.org, retrieved Nov. 16, 2023, pp. 1-12.

"Random forest", Wikipedia.org, retrieved Nov. 16, 2023, pp. 1-13.

"Support vector machine", Wikipedia.org, retrieved Nov. 16, 2023, pp. 1-13.

"Training, validation, and test data sets", retrieved Nov. 16, 2023, pp. 1-6.

"XGBoost", Wikipedia.org, retrieved Nov. 16, 2023, pp. 1-4.

"Artifical neural network", Wikipedia.org, retrieved Nov. 16, 2023, pp. 1-38.

"Autoregressive model", Wikipedia.org, retrieved Nov. 16, 2023, pp. 1-12.

"BERT (language model)", Wikipedia.org, retrieved Nov. 16, 2023, pp. 1-6.

"CatBoost", Wikipedia.org, retrieved Nov. 16, 2023, pp. 1-3.

"Decision tree learning", Wikipedia.org, retrieved Nov. 16, 2023, pp. 1-12.

"Decomposition of time series", Wikipedia.org, retrieved Nov. 16, 2023, pp. 1-3.

"Deep learning", Wikipedia.org, retrieved Nov. 16, 2023, pp. 1-45.

"Ensemble learning", Wikipedia.org, retrieved Nov. 16, 2023, pp. 1-15.

"Feedforward neural network", Wikipedia. org, retrieved Nov. 16, 2023, pp. 1-7.

"Gated recurrent unit", Wikipedia.org, retrieved Nov. 16, 2023, pp. 1-4.

"Gradient boosting", Wikipedia.org, retrieved Nov. 16, 2023, pp. 1-10.

"K-nearest neighbors algorithm", Wikipedia.org, retrieved Nov. 16, 2023, pp. 1-11.

"Cluster analysis", Wikipedia.org, retrieved Nov. 20, 2023, pp. 1-22.

International Search Report and Written Opinion received for PCT Patent Application No. PCT/US2020/034561, mailed on Jul. 28, 2020, pp. 1-11.

Extended European Search Report received for European Application No. 20938380.1, mailed on Nov. 30, 2023, pp. 1-5.

Non-Final Office Action for related U.S. Appl. No. 17/999,045 dated Jul. 2, 2024, pp. 1-44.

Artificial Intelligence-Enhanced Predictive Insights for Advancing Financial Inclusion: A Human-CentricAI-Thinking ApproachMeng-Leong How; Sin-Mei Cheah; Khor, Aik Cheow; Chan, Yong Jiet. Big Data and Cognitive Computing4.2:8. MDPI AG (2020), 13 pages.

Non-Final Office Action for U.S. Appl. No. 18/516,354 dated Dec. 17, 2024, pp. 1-31.

Final Office Action for U.S. Appl. No. 17/999,045 dated Feb. 12, 2025, pp. 1-29.

International Search Report and Written Opinion for application PCT/US2023/080751, pp. 1-11.

International Search Report and Written Opinion for application PCT/US2023/080231, pp. 1-13.

(56) References Cited

OTHER PUBLICATIONS

International Search Report and Written Opinion for application PCT/US2023/076284, pp. 1-13.
International Search Report and Written Opinion for Int'l Application No. PCT/US2024/039962 dated Apr. 14, 2025, pp. 1-14.
International Search Report and Written Opinion for Int'l Application No. PCT/US2024/035455 dated Mar. 19, 2025, pp. 1-11.
Final Office Action for U.S. Appl. No. 18/516,354 dated Jun. 9, 2025, pp. 1-20.
Non-Final Office Action for U.S. Appl. No. 17/999,045 dated Jun. 30, 2025, pp. 1-26.
Non-Final Office Action for U.S. Appl. No. 18/786,540 dated Sep. 11, 2025, pp. 1-48.
Office Action for CN Application No. 202080101992.0 dated Feb. 26, 2025, pp. 1-4. (Non-English).
Office Action for CN Application No. 202080101992.0 dated Jul. 30, 2025, pp. 1-9. (Non-English).
P. Ongsulee, V. Chotchaung, E. Bamrungsi and T. Rodcheewit, "Big Data, Predictive Analysis and Machine Learning," 2018 16th International Conference on ICT and Knowledge Engineering (ICT &KE), Bangkok, Thailand, 2018, pp. 1-6.

* cited by examiner

900a

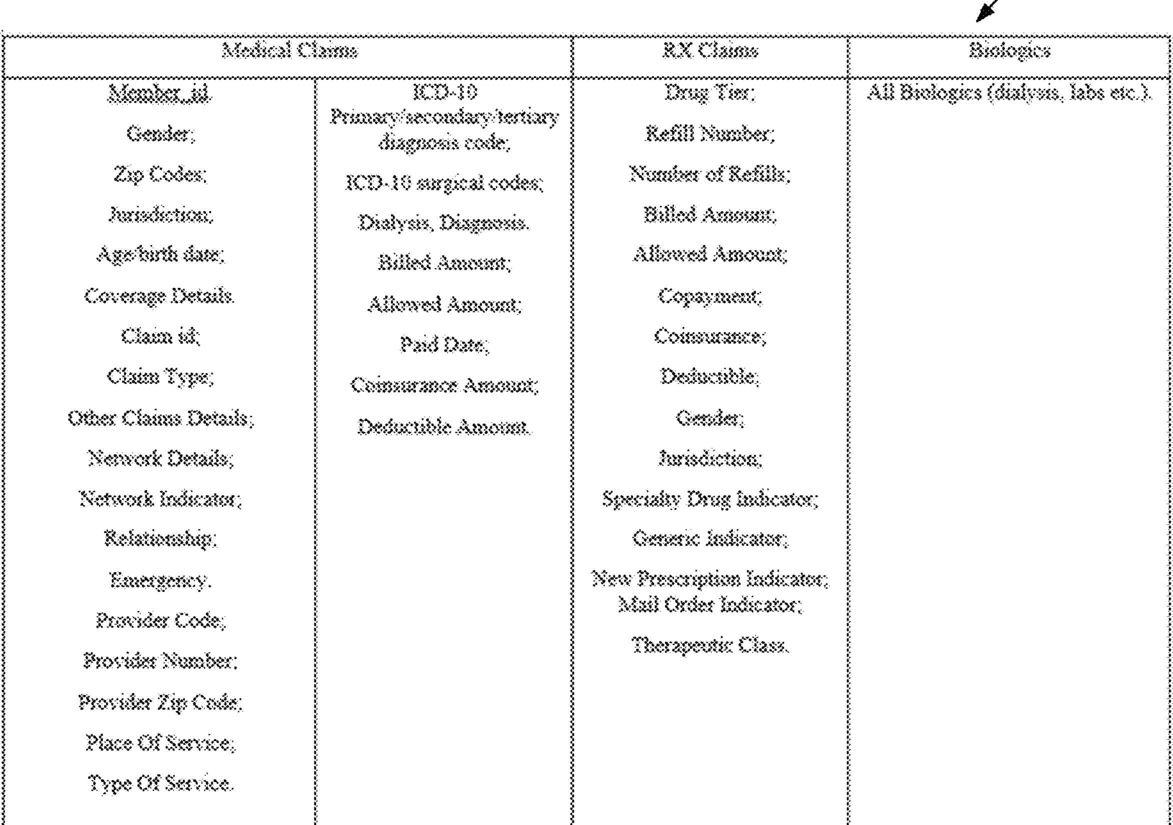

| Medical Claims | | RX Claims | Biologics |
|---|---|---|---|
| Member_id | ICD-10 Primary/secondary/tertiary diagnosis code; | Drug Tier; | All Biologics (dialysis, labs etc.). |
| Gender; | ICD-10 surgical codes; | Refill Number; | |
| Zip Codes; | Dialysis, Diagnosis. | Number of Refills; | |
| Jurisdiction; | Billed Amount; | Billed Amount; | |
| Age/birth date; | Allowed Amount; | Allowed Amount; | |
| Coverage Details. | Paid Date; | Copayment; | |
| Claim id; | Coinsurance Amount; | Coinsurance; | |
| Claim Type; | Deductible Amount. | Deductible; | |
| Other Claims Details; | | Gender; | |
| Network Details; | | Jurisdiction; | |
| Network Indicator; | | Specialty Drug Indicator; | |
| Relationship; | | Generic Indicator; | |
| Emergency. | | New Prescription Indicator; Mail Order Indicator; | |
| Provider Code; | | Therapeutic Class. | |
| Provider Number; | | | |
| Provider Zip Code; | | | |
| Place Of Service; | | | |
| Type Of Service. | | | |

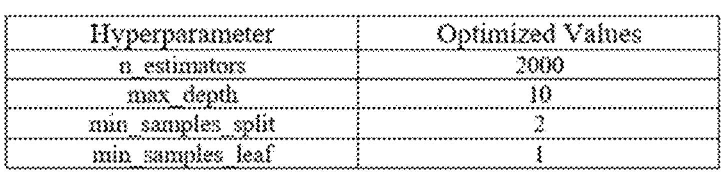

| Hyperparameter | Optimized Values |
|---|---|
| n_estimators | 2000 |
| max_depth | 10 |
| min_samples_split | 2 |
| min_samples_leaf | 1 |

FIG. 9B

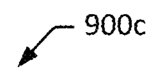

| Module | List of Attributes |
| --- | --- |
| CKD transitions | Patient ID;<br>Occupation;<br>Marital Status;<br>Tobacco Usage;<br>Drug Usage;<br>Relationship to Subscriber;<br>Company Type;<br>Plan Type;<br>Provider Type;<br>Provider Specialty;<br>Primary Diagnosis;<br>Secondary Diagnosis;<br>Other Diagnosis;<br>Hospitalizations;<br>Type of Service;<br>Procedures, Transplants;<br>Dialysis;<br>Allowed Amount;<br>Billed Amount;<br>Coinsurance Amount;<br>Copayment;<br>Net Paid Amount;<br>Claim Type, Network Status;<br>Claim Benefits, Drug Names;<br>Drug Frequency;<br>Drug Strength, Drug Type;<br>Days Supplied;<br>Administration Route;<br>OTC/Prescription;<br>Pick-up/Delivery;<br>Pharmacy Type;<br>Pharmacy Network Status. |

FIG. 9C

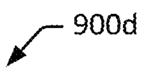

| Module | NBA | List of Attributes |
| --- | --- | --- |
| Next Best Action Recommendation | Hospitalization | 'Alchohol_No', 'Alchohol_Yes', 'BPSitting_Diastolic_Diff', 'BPSitting_Diastolic_Pre', 'BPSitting_Systolic_Diff', 'BPSitting_Systolic_Pre', 'BPStanding_Diastolic_Diff', 'BPStanding_Diastolic_Pre', 'BPStanding_Systolic_Diff', 'BPStanding_Systolic_Pre', 'BloodSugar_Diff', 'BloodSugar_Pre', 'Diagnosis_Diabetes', 'Diagnosis_Hypertension', 'Diagnosis_Ischemia', 'DryWeight', 'Height', 'Language_English', 'MaritalStatus_0', 'MaritalStatus_Divorced', 'MaritalStatus_Married', 'MaritalStatus_Separated', 'MaritalStatus_Single', 'MaritalStatus_Widowed', 'PlannedHospitalization_No', 'PlannedHospitalization_Yes', 'PulseSitting_Diff', 'PulseSitting_Pre', 'PulseStanding_Diff', 'PulseStanding_Pre', 'RespiratoryRate_Diff', 'RespiratoryRate_Pre', 'ShortnessOfBreath_No', 'ShortnessOfBreath_Yes', 'Smoking_No', 'Smoking_Yes', 'Temperature_Diff', 'Temperature_Pre', 'TreatmentTypeName_Extra_Treatment', 'TreatmentTypeName_Home_Hemo_Dialysis', 'TreatmentTypeName_In_Center_Hemo_Dialysis', 'TreatmentTypeName_No_Show', 'TreatmentTypeName_Peritoneal', 'Weight_Diff', 'Weight_Pre' |

FIG. 9D

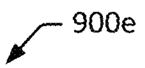

| Module | NBA | List of Attributes |
|---|---|---|
| Next Best Action Recommendation | Appointment No-Shows | 'ACE_Medication', 'ARB_Medication', 'Alchohol_No', 'Alchohol_Yes', 'BillingCharge', 'Credit_Amount', 'Diabetes_Diag', 'Diabetes_Hosp_Diag', 'English_Language', 'Gender_F', 'Gender_M', 'Hypertension_Diag', 'Hypertension_Hosp_Diag', 'InitialExpectedPayment', 'Ischemia_Diag', 'Ischemia_Hosp_Diag', 'MaritalStatus_0', 'MaritalStatus_Divorced', 'MaritalStatus_Married', 'MaritalStatus_Separated', 'MaritalStatus_Single', 'MaritalStatus_Widowed', 'MedicareApprovedCoinsAmt', 'PatientResponsibleAmt', 'PlannedHospitalization_No', 'PlannedHospitalization_Yes', 'SGLT2_Medication', 'Smoking_No', 'Smoking_Yes', 'TotalAdjustment', 'TotalAllowedAmt', 'TotalCredit', 'TotalSubmittedAmt'] |

| Module | NBA | List of Attributes |
| --- | --- | --- |
| Next Best Action Recommendation | Adequacy | 'Age', 'DialysisAge', 'MaritalStatus_0', 'MaritalStatus_Divorced', 'MaritalStatus_Married', 'MaritalStatus_NULL', 'MaritalStatus_Separated', 'MaritalStatus_Single', 'MaritalStatus_Unknown', 'MaritalStatus_Widowed', 'Language_Other', 'Language_eng-English', 'Gender_F', 'Gender_M', 'Smoking_No', 'Smoking_Yes', 'Alchohol_No', 'Alchohol_Yes', 'year', 'month', 'NumOf Home Hemo Dialysis', 'NumOf No Show', 'NumOf Peritoneal', 'NumOf In-Center Hemo Dialysis', 'NumOf Extra Treatment', 'Pre_PulseSitting', 'Post_BPSitting', 'Pre_BPSitting', 'Pre_Lungs_Clear', 'Pre_Lungs_NoClear', 'Pre_Appetite_Fair', 'Pre_Appetite_Good', 'Pre_Appetite_NULL', 'Pre_Appetite_Poor', 'Pre_LEEdema_1+', 'Pre_LEEdema_2+', 'Pre_LEEdema_3+', 'Pre_LEEdema_4+', 'Pre_LEEdema_NULL', 'Pre_LEEdema_None', 'Pre_PeriorbiutalEdema_Mild', 'Pre_PeriorbiutalEdema_Moderate Severe', 'Pre_PeriorbiutalEdema_NULL', 'Pre_PeriorbiutalEdema_No', 'Pre_PedalEdema_1+', 'Pre_PedalEdema_2+', 'Pre_PedalEdema_3+', 'Pre_PedalEdema_4+', 'Pre_PedalEdema_NULL', 'Pre_FacialEdema_Mild', 'Pre_FacialEdema_Moderate Severe', 'Pre_FacialEdema_NULL', 'Pre_FacialEdema_No', 'Pre_Diarrhea_Mild', 'Pre_Diarrhea_Moderate', 'Pre_Diarrhea_NULL', 'Pre_Diarrhea_None', 'Pre_Diarrhea_Severe', 'Pre_Nausea_Mild', 'Pre_Nausea_Moderate', 'Pre_Nausea_NULL', 'Pre_Nausea_None', 'Pre_Nausea_Severe', 'Pre_ShortnessOfBreath_No', 'Pre_ShortnessOfBreath_Yes', 'Pre_HeartRhythm_Irregular', 'Pre_HeartRhythm_NULL', 'Pre_HeartRhythm_Regular', 'avg BUN', 'avg BUN, Post', 'avg Hemoglobin', 'avg Potassium', 'avg Sodium', 'avg Phosphorus', 'avg Creatinine', 'avg Transferrin Sat (Calc)', 'avg Calcium', 'urr_target |

| Module | NBA | List of Attributes |
| --- | --- | --- |
| Next Best Action Recommendation | Dry weight prediction | 'Age', 'DialysisAge', 'MaritalStatus_0', 'MaritalStatus_Divorced', 'MaritalStatus_Married', 'MaritalStatus_NULL', 'MaritalStatus_Separated', 'MaritalStatus_Single', 'MaritalStatus_Unknown', 'MaritalStatus_Widowed', 'Language_Other', 'Language_eng-English', 'Gender_F', 'Gender_M', 'Smoking_No', 'Smoking_Yes', 'Alchohol_No', 'Alchohol_Yes', 'year', 'month', 'NumOf Home Hemo Dialysis', 'NumOf No Show', 'NumOf Peritoneal', 'NumOf In-Center Hemo Dialysis', 'NumOf Extra Treatment', 'Pre_PulseSitting', 'Post_BPSitting', 'Pre_BPSitting', 'Pre_Lungs_Clear', 'Pre_Lungs_NoClear', 'Pre_Appetite_Fair', 'Pre_Appetite_Good', 'Pre_Appetite_NULL', 'Pre_Appetite_Poor', 'Pre_LEEdema_1+', 'Pre_LEEdema_2+', 'Pre_LEEdema_3+', 'Pre_LEEdema_4+', 'Pre_LEEdema_NULL', 'Pre_LEEdema_None', 'Pre_PeriorbiutalEdema_Mild', 'Pre_PeriorbiutalEdema_Moderate Severe', 'Pre_PeriorbiutalEdema_NULL', 'Pre_PeriorbiutalEdema_No', 'Pre_PedalEdema_1+', 'Pre_PedalEdema_2+', 'Pre_PedalEdema_3+', 'Pre_PedalEdema_4+', 'Pre_PedalEdema_NULL', 'Pre_FacialEdema_Mild', 'Pre_FacialEdema_Moderate Severe', 'Pre_FacialEdema_NULL', 'Pre_FacialEdema_No', 'Pre_Diarrhea_Mild', 'Pre_Diarrhea_Moderate', 'Pre_Diarrhea_NULL', 'Pre_Diarrhea_None', 'Pre_Diarrhea_Severe', 'Pre_Nausea_Mild', 'Pre_Nausea_Moderate', 'Pre_Nausea_NULL', 'Pre_Nausea_None', 'Pre_Nausea_Severe', 'Pre_ShortnessOfBreath_No', 'Pre_ShortnessOfBreath_Yes', 'Pre_HeartRhythm_Irregular', 'Pre_HeartRhythm_NULL', 'Pre_HeartRhythm_Regular', 'avg BUN', 'avg BUN, Post', 'avg Hemoglobin', 'avg Potassium', 'avg Sodium', 'avg Phosphorus', 'avg Creatinine', 'avg Transferrin Sat (Calc)', 'avg Calcium', 'urr_target |

FIG. 9G

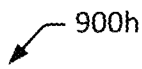

| Module | NBA | List of Attributes |
|---|---|---|
| Next Best Action Recommendation | Anemia | 'Age', 'DialysisAge', 'MaritalStatus_0', 'MaritalStatus_Divorced', 'MaritalStatus_Married', 'MaritalStatus_NULL', 'MaritalStatus_Separated', 'MaritalStatus_Single', 'MaritalStatus_Unknown', 'MaritalStatus_Widowed', 'Language_Other', 'Language_eng-English', 'Gender_F', 'Gender_M', 'Smoking_No', 'Smoking_Yes', 'Alchohol_No', 'Alchohol_Yes', 'year', 'month', 'NumOf Home Hemo Dialysis', 'NumOf No Show', 'NumOf Peritoneal', 'NumOf In-Center Hemo Dialysis', 'NumOf Extra Treatment', 'Pre_PulseSitting', 'Post_BPSitting', 'Pre_BPSitting', 'Pre_Lungs_Clear', 'Pre_Lungs_NoClear', 'Pre_Appetite_Fair', 'Pre_Appetite_Good', 'Pre_Appetite_NULL', 'Pre_Appetite_Poor', 'Pre_LEEdema_1+', 'Pre_LEEdema_2+', 'Pre_LEEdema_3+', 'Pre_LEEdema_4+', 'Pre_LEEdema_NULL', 'Pre_LEEdema_None', 'Pre_PeriorbiutalEdema_Mild', 'Pre_PeriorbiutalEdema_Moderate Severe', 'Pre_PeriorbiutalEdema_NULL', 'Pre_PeriorbiutalEdema_No', 'Pre_PedalEdema_1+', 'Pre_PedalEdema_2+', 'Pre_PedalEdema_3+', 'Pre_PedalEdema_4+', 'Pre_PedalEdema_NULL', 'Pre_FacialEdema_Mild', 'Pre_FacialEdema_Moderate Severe', 'Pre_FacialEdema_NULL', 'Pre_FacialEdema_No', 'Pre_Diarrhea_Mild', 'Pre_Diarrhea_Moderate', 'Pre_Diarrhea_NULL', 'Pre_Diarrhea_None', 'Pre_Diarrhea_Severe', 'Pre_Nausea_Mild', 'Pre_Nausea_Moderate', 'Pre_Nausea_NULL', 'Pre_Nausea_None', 'Pre_Nausea_Severe', 'Pre_ShortnessOfBreath_No', 'Pre_ShortnessOfBreath_Yes', 'Pre_HeartRhythm_Irregular', 'Pre_HeartRhythm_NULL', 'Pre_HeartRhythm_Regular', 'avg BUN', 'avg BUN, Post', 'avg Hemoglobin', 'avg Potassium', 'avg Sodium', 'avg Phosphorus', 'avg Creatinine', 'avg Transferrin Sat (Calc)', 'avg Calcium', 'urr_target |

FIG. 9H

MEDICAL CARE MANAGEMENT SYSTEM AND METHOD

FIELD

Embodiments relate generally to medical care, and more particularly to patient diagnosis decision support and treatment.

BACKGROUND

Early detection and prediction of diseases can play a pivotal role in preventive healthcare. Timely intervention can reduce morbidity, improve patient outcomes, and lead to more cost-effective healthcare management. Unfortunately, traditional forms of patient diagnosis and treatment are often limited in scope and can be untimely. For example, patient diagnostics may rely on a health care provider's individual interpretation of a limited amount of patient information, based on personal experience and opinion. Thus, existing techniques may fail to accurately characterize and diagnose patients and may not be capable of providing timely assessments and treatments that reflect holistic views of patients.

SUMMARY

Provided in certain embodiments are novel techniques for obtaining, processing and employing patient data for use in assisting diagnosing decision support and treating patients. As described, such techniques may provide for integration of a multitude of healthcare related data sources—whether structured, unstructured, or semi-structured—which can, in turn, provide assistance in diagnosis decision support and treatment of patients based on a holistic view of patients (and associated data). Such techniques may be utilized to craft and implement, for example, patient specific diagnosis reports and treatment plans. Further, the techniques described may help to reduce the time required for diagnosis and treatment, in some instances providing real-time diagnosis and treatment (e.g., in a matter of hours or days, as opposed to months or years).

Volume, variety, and quality of healthcare data can be central to data driven healthcare, including diagnosis and treatment of patients based on relevant healthcare data. Unfortunately, there are no well-defined and/or unique ways of capturing and storing healthcare data across the organizations. For example, data can exist in structured or in unstructured formats that are difficult to reconcile across platforms. Further, it is often critical that healthcare be compliant with associated healthcare regulations. As a result, certain data processing techniques are directed to data extraction, transformation, and loading ("ETL"). To some extent these are helpful for data preparation (particularly for structured data elements) but often lack the capabilities for advanced techniques, such as artificial intelligence ("AI") based modeling, or the like. Although certain techniques may provide mechanisms for ETL or AI modeling, there are often at least two significant problems: (1) the techniques are generic in that their functionalities are common across all the industries, which may not be suitable for highly regulated industries (such as healthcare and finance); and (2) the techniques are generally not designed to provide the actionable recommendations which can directly impact business operations, ROI, interventions in healthcare management, or the like.

Provided in some embodiments are methods for identifying and employing healthcare data and parameters. For example, a healthcare process in accordance with embodiments described here may include the following: (1) obtaining a set of historical healthcare data (e.g., including patient data); (2) determining one or more healthcare models based on the set of historical healthcare data; (3) determining a healthcare report (e.g., a patient report) for a patient based on application of healthcare data for the patient to the one or more healthcare models; (4) determining one or more parameters for treatment of the patient based on the healthcare report; (5) determining a patient treatment plan ("PTP") based on the one or more parameters; and (6) treating the patient in accordance with the PTP. In some instances, obtaining a set of historical healthcare data includes obtaining various types of historical healthcare data (e.g., including structured and unstructured patient data indicative of various characteristics of any number of persons) from a variety of sources (e.g., from healthcare facilities, healthcare data aggregators, healthcare providers, health care insurers, healthcare studies, or the like). As described, techniques may be employed to integrate the historical healthcare data into a training dataset that can be used to train associated healthcare models. In some embodiments, determining one or more healthcare models based on a set of historical healthcare data includes training one or more healthcare models, such as those described here, using the set of historical healthcare data. As described, in some instances, these models may be retrained (or "updated") over time as the set of historical patient data is updated (e.g., as new healthcare data is populated). In some embodiments, determining a healthcare report for a patient based on application of patient data to the one or more healthcare models includes applying data for one or more patients, such as characteristics specific to the individual patient (or associated patients), to one or more of the models. Such a healthcare report may include determinations regarding the state of the patient, such as current condition, associated diagnosis, associated classifications, or the like. In some embodiments, determining one or more parameters for treatment of the patient based on the healthcare report includes determining one or more treatment parameters, such as parameters defining actions to be taken to treat the patient. This may include, for example, suggestions for observation, check-ups with healthcare practitioners, procedures to undergo, or the like, and timing/scheduling such as frequency of actions, time-frames of action, dates for action, or the like. In some embodiments, determining a PTP based on one or more parameters may include generating a treatment plan for a patient that is based on the one or more parameters determined. For example, a PTP for a patient may include an exercise plan for a patient, scheduling of visits to one or more healthcare professionals, scheduling of one or more procedures or the like. In some embodiments, determining a PTP based on one or more parameters includes employing custom parameters for a patient that are tailored to generate a specific plan based on the patient's specific needs. In some embodiments, treating a patient in accordance with the parameters or the PTP may include executing or otherwise providing treatment in accordance with the PTP. For example, this may include a healthcare system scheduling and tracking a patient's exercise, healthcare office visits or healthcare procedures, or the like.

Although certain embodiments are described in the context of generating a comprehensive patient report through the analysis of multiple trained interlinked machine learning models, such an environment may be employed in any suitable context, such as other forms of assessing patient conditions, diagnosis and treatment.

BRIEF DESCRIPTION OF THE DRAWINGS

FIGS. 9A-9H are diagrams that illustrate various inputs and parameters in accordance with one or more embodiments.

Figure 1A:
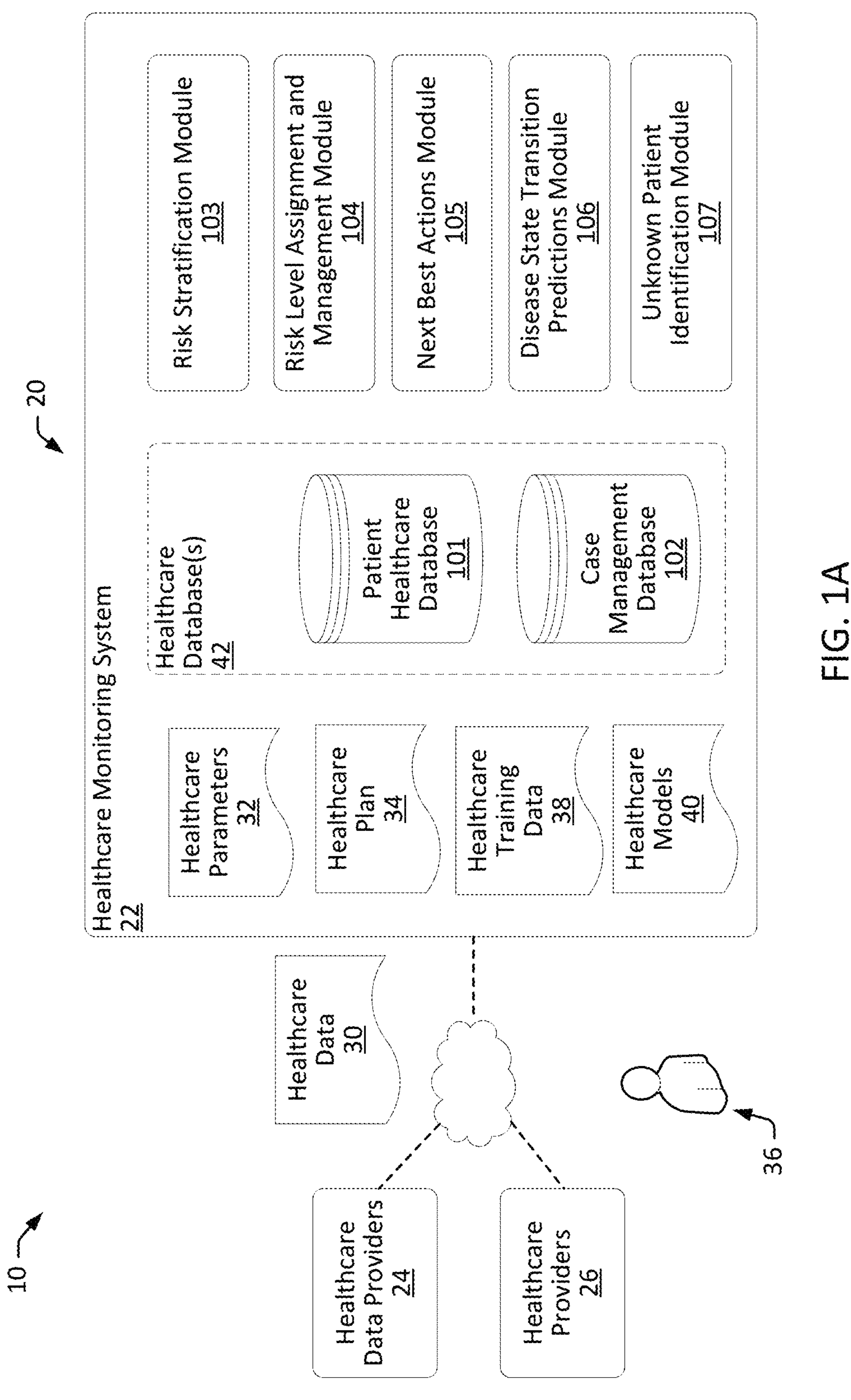
FIGS. 1A and 1B are diagrams that illustrate a medical management environment in accordance with one or more embodiments.

While this disclosure is susceptible to various modifications and alternative forms, specific example embodiments are shown and described. The drawings may not be to scale. It should be understood that the drawings and the detailed description are not intended to limit the disclosure to the particular form disclosed, but are intended to disclose modifications, equivalents, and alternatives falling within the spirit and scope of the present disclosure as defined by the claims.

DETAILED DESCRIPTION OF THE DRAWINGS

Provided in certain embodiments are novel techniques for obtaining, processing and employing patient data for use in diagnosing and treating patients. As described, such techniques may provide for integration of a multitude of healthcare related data sources—whether structured, unstructured, or semi-structured—which can, in turn, provide diagnosis and treatment of patients based on a holistic view of patients (and associated data). Such techniques may be utilized to craft and implement, for example, patient specific diagnosis reports and treatment plans. Further, the techniques described may help to reduce the time required for diagnosis and treatment, in some instances providing real-time diagnosis and treatment (e.g., in a matter of seconds, minutes, hours or days, as opposed to months or years).

Provided in some embodiments are methods for identifying and employing healthcare data and parameters. For example, a healthcare process in accordance with embodiments described here may include the following: (1) obtaining a set of historical healthcare data (e.g., including patient data); (2) determining one or more healthcare models based on the set of historical healthcare data; (3) determining a healthcare report (e.g., a patient report) for a patient based on application of healthcare data for the patient to the one or more healthcare models; (4) determining one or more parameters for treatment of the patient based on the healthcare report; (5) determining a patient treatment plan ("PTP") based on the one or more parameters; and (6) treating the patient in accordance with the PTP. In some instances, obtaining a set of historical healthcare data includes obtaining various types of historical healthcare data (e.g., including structured and unstructured patient data indicative of various characteristics of any number of persons) from a variety of sources (e.g., from healthcare facilities, healthcare data aggregators, healthcare providers, health care insurers, healthcare studies, or the like). As described, techniques may be employed to integrate the historical healthcare data into a training dataset that can be used to train associated healthcare models. In some embodiments, determining one or more healthcare models based on a set of historical healthcare data includes training one or more healthcare models, such as those described here, using the set of historical healthcare data. As described, in some instances, these models may be retrained (or "updated") over time as the set of historical patient data is updated (e.g., as new healthcare data is populated). In some embodiments, determining a healthcare report for a patient based on application of patient data to the one or more healthcare models includes applying data for one or more patients, such as characteristics specific to the individual patient (or associated patients), to one or more of the models. Such a healthcare report may include determinations regarding the state of the patient, such as current condition, associated diagnosis, associated classifications, or the like. In some embodiments, determining one or more parameters for treatment of the patient based on the healthcare report includes determining one or more treatment parameters, such as parameters defining actions to be taken to treat the patient. This may include, for example, suggestions for observation, check-ups with healthcare practitioners, procedures to undergo, or the like, and timing/scheduling such as frequency of actions, timeframes of action, dates for action, or the like. In some embodiments, determining a PTP based on one or more parameters may include generating a treatment plan for a patient that is based on the one or more parameters determined. For example, a PTP for a patient may include an exercise plan for a patient, scheduling of visits to one or more healthcare professionals, scheduling of one or more procedures or the like. In some embodiments, determining a PTP based on one or more parameters includes employing custom parameters for a patient that are tailored to generate a specific plan based on the patient's specific needs. In some embodiments, treating a patient in accordance with the parameters or the PTP may include executing or otherwise providing treatment in accordance with the PTP. For example, this may include a healthcare system scheduling and tracking a patient's exercise, healthcare office visits or healthcare procedures, or the like.

In some embodiments, described are techniques for generating patient reports that employ a suite of machine learning modules trained using an array of healthcare related data sources. In some embodiments, the technique initiates with the collection of patient-specific data, such as patient medical histories, test results, medications, and no-show appointments. As described, the patient-specific data can serve as an input source for downstream custom-built machine learning applications, such as a risk stratification module, a risk management module, a disease state transition predictions module, a hospitalization module, or the like. In some embodiments, natural language processing or additional data science tools, are incorporated to provide a comprehensive healthcare reporting system. The outcomes derived from the machine learning models may, for example, be channeled into dynamic applications, such as Next Best Action ("NBA") module, offering actionable recommendations like prescription refills, provider switches, or health plan adjustments.

Once optimized, these models may function as AI-driven risk stratification engines, automatically identifying risk pathways for both existing and new patients. Although certain embodiments are described in the context of healthcare for the purpose of explanation, such techniques may be employed in various context, such as for empowering businesses to craft targeted intervention strategies. For example, data processing pipelines may pull information from various sources, including data warehouses, cloud, or on-premises storage, and through APIs. This data could then be consolidated based on a unique identifier, typically the patient identifier ("ID").

With regard to generating a patient report, as described, this may include a specialized process for obtaining and employing healthcare data. In some embodiments, such a process commences by acquiring an extensive dataset of patient healthcare information. Subsequent to this acquisition, a series of machine learning models are trained, enhancing their precision iteratively. Once trained, these models are deployed to analyze an individual patient's unique healthcare data (e.g., patient data), thereby generating a customized diagnosis report tailored specifically to that patient. Certain embodiments may include generating a personalized diagnosis report for individuals afflicted with various conditions, such as End Stage Renal Disease ("ESRD"), Chronic kidney disease ("CKD"), Cardiovascular disease ("CVD"), Diabetes, pre diabetes, mental health, Chronic obstructive pulmonary disease ("COPD"), or the like. Such a report may be formulated by analyzing a curated set of patient specific healthcare data and attributes associated with one or more conditions using a suite of machine learning models. These models may be meticulously trained to evaluate risk factors, discern disease stage transitions, recommend subsequent optimal actions, and conduct other pertinent health evaluations. Although certain embodiments are described in the context of certain conditions, such as ESRD, for the purpose of illustration, embodiments may be employed in any suitable context, such as for CKD, CVD, Diabetes, pre diabetes, mental health, COPD, or the like.

Figure 1B:
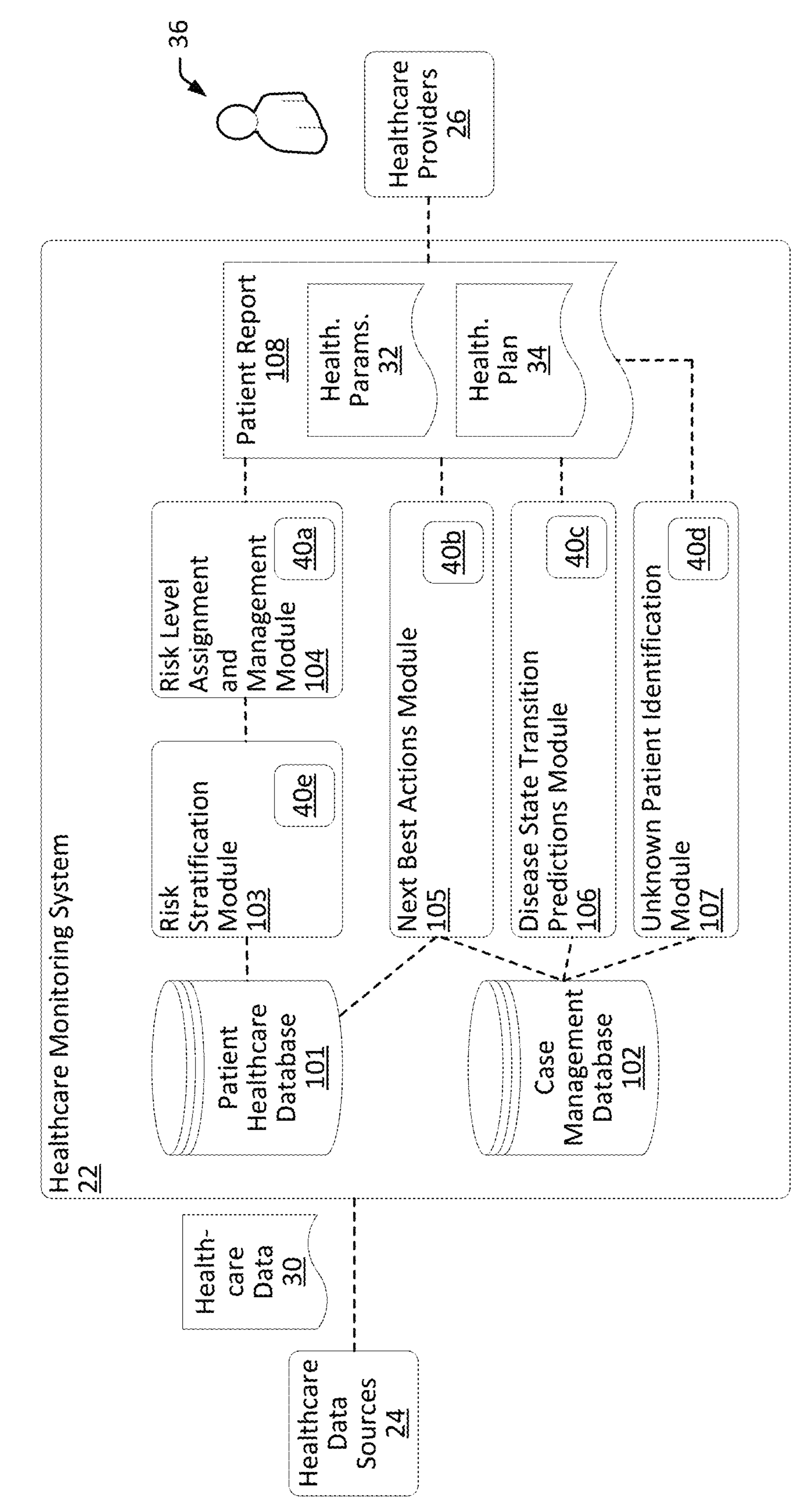

FIGS. 1A and 1B are diagrams that illustrate a healthcare environment 10 in accordance with one or more embodiments. In the illustrated embodiment, the environment 10 includes a healthcare system 20 that includes a healthcare monitoring system 22, healthcare data providers 24, and healthcare providers 26.

In some embodiments, the healthcare monitoring system 22 is operable to obtain and process healthcare data 30 to determine and employ associated healthcare parameters 32 or healthcare plans 34 (e.g., patient treatment plans (PTPs)). A healthcare plan 34 for a given patient 36 may include a set of one or more healthcare parameters 32 that define treatment of the patient 36. Such a plan may define actions (e.g., next best actions ("NBAs")) to be employed for treating the patient 36. In some embodiments, the healthcare monitoring system 22 includes or otherwise employs a computer system that is the same as or similar to computer system 1000 described with regard to at least FIG. 10.

In some embodiments, healthcare data provider 24 includes one or more sources of healthcare data 30. This may include one or more healthcare facilities, such as hospitals, treatments centers, or the like, other sources of healthcare data 30, such healthcare data aggregators, healthcare providers, health care insurers, healthcare research facilities, or the like. For instance, the healthcare data provider 24 may be a research institution housing patient data related to clinical trials, or a rehabilitation center maintaining records of patient check-ins and check-outs. In some embodiments, the healthcare data provider(s) 24 include or otherwise employs a computer system that is the same as or similar to computer system 1000 described with regard to at least FIG. 10.

In some embodiments, healthcare data 30 includes data indicative of characteristics of one or more patients 34. For example, healthcare data 30 may include patient demographics (e.g., age, gender, ethnicity), medical history (e.g., previous diagnoses, surgeries, allergies), current medications, lab results, radiology images, genetic information, lifestyle factors (e.g., smoking status, alcohol consumption), and wearables data (e.g., heart rate, step count) or the like for one or more patients.

As described healthcare training data 38 may be a subset of healthcare data 30. Such healthcare training datasets 38 may be used for training (or re-training) healthcare models 40. For example, as described, the healthcare monitoring system 22 may obtain healthcare data 30, extract healthcare training data 38 from the healthcare data 30, train a healthcare model 40 using the training healthcare data 38, and apply the trained healthcare model 40 to other portions of the healthcare data 30 associated with one or more patients 36 to determine healthcare parameters 32 (and a healthcare plan 34) that define next best actions for treatment of the one or more patients 36. As described, as updated healthcare data 30 is obtained, "updated" training healthcare datasets 38 may be identified and used to "update" (or "re-train") healthcare models 40. In some embodiments, retraining of a model is conducted in response to a given event, such as expiration of a period of time (e.g., daily, weekly, monthly, annually, etc.), results exceeding an accuracy tolerance (e.g., when accuracy drifts below a prescribed level), or the like.

In some embodiments, healthcare providers 26 include persons, facilities, systems, or the like that provide healthcare services to patients. For example, healthcare providers 26 may include physicians, therapists, nurses, hospitals, treatments centers, healthcare systems, or the like that provide healthcare services to patients 36. As described here, healthcare providers 26 may provide healthcare services to patients in accordance with associated healthcare parameters 32 or healthcare plans (e.g., patient treatment plans (PTPs)). For example, a healthcare provider 26 may provide healthcare services to the patient 36 in accordance with healthcare parameters 32 (or a healthcare plan 34), determined for the patient 36 based on an application of a portion of current healthcare data 30 associated with the patient 30, to a healthcare model 40 trained using healthcare training data 38 extracted from historical healthcare data 30 for the patient 36 or other persons. In some embodiments, the healthcare provider(s) 26 include or otherwise employs a computer system that is the same as or similar to computer system 1000 described with regard to at least FIG. 10.

In some embodiments, the healthcare monitoring system 22 includes one or more healthcare databases 42. For example, in the illustrated embodiment, the healthcare monitoring system 22 includes healthcare databases 42 that include a patient healthcare database 101 and a case management database 102. These databases 101 and 102 may store associated portions of the healthcare data 30 and be accessible by various modules performing analytical evaluations on the data therein. For example, the patient healthcare database 101 may store a portion of the healthcare data 30 that includes patient healthcare data indicative of the patient's medical history and treatment pattern, such as medical claims, prescription claims, biologics, or the like. The case management database 102 may store a portion of the healthcare data 30 that includes patient case data that is indicative of the patient's care plan details and progress, such as patient demographics, medical history, medication information, treatment plans, appointment logs, patient communications, or the like. In some embodiments, the databases described herein may be configured to be separate or combined as a single unified database. For example, the patient healthcare database 101 may be one of the same as the case management database 102. Further, data may also be co-located across various databases throughout an environment. Although certain embodiments are described in the context of various types of data stored on certain databases for the purpose of explanation, embodiments may include any suitable source of healthcare data 30 regarding patients (e.g., geography, data about the geography, and data about the healthcare provider, obtained from any suitable source, or the like), and the various types of healthcare data 30 may be stored on the same or separate databases.

As described, in some embodiments, the risk stratification module 103 obtains from the patient healthcare database 101, relevant patient characteristic data and processes the obtained data to generate a risk stratification assessment, which may include one or both a patient stratification score and a binary classification for a patient. The patient stratification score may be indicative of a patient's susceptibility to developing high-risk diseases. The binary classification may be indicative of whether patient's healthcare billed amounts are following an upward or downward trajectory. Subsequently, the risk level assignment and management module 104 may obtain from the risk stratification module 103, the determined patient stratification score and binary classification (and obtain other pertinent information from the patient healthcare database 101) and process the obtained information to produce an output defining a risk level assignment for the patient, which may, for example, be inclusive of a risk level score and a categorization of the patient's risk. The risk level assignment and management module 104 may convey one or both of the input obtained from the risk stratification module 103 and its output to be integrated into a patient report 108, which may be assembled by the healthcare monitoring system 22. As described, other modules, including some or all of a next best actions module 105, a disease state transition predictions module 106, and an unknown patient identification module 107 may obtain their respective sets of input data from the case management database 102. The next best actions module 105 may obtain input data from the case management database 102 and process the input data to determine a series of recommended patient actions, which may, for example, encompass a patient outcome prediction. The disease state transition predictions module 106 may obtain input data from the case management database 102 and process the input data to determine a patient disease state transition prediction, which may, for example, include transition probabilities pertinent to a respective patient. The unknown patient identification module 107 may obtain input data from the case management database 102 and process the input data to determine a prediction on unidentified patient data, possibly featuring a disease propensity score for the patient. The collective outputs—recommended actions from module 105, disease transition prediction from module 106, and unknown patient identification prediction from module 107—may, for example, be seamlessly consolidated into a comprehensive patient report 108.

In some embodiments, the risk level assignment and management module 104 employs a trained risk level assignment and management model 40*a*. Training of the model 40*a* may include training based on historical healthcare data from a second healthcare database. This collected data may comprise of both structured historical healthcare data and unstructured historical healthcare data. A pivotal aspect of this training may revolve around the generation of a multi-class risk level classifier. To form this classifier, the system may evaluate the historical healthcare patient data for one or more patients 36 in tandem with the patients' respective binary classifications, identifying essential risk features that are associated with respective binary classifications. Consequently, this multi-class risk level classifier may incorporate these key risk features. The risk level assignment and management module 104 employs the trained risk level assignment and management model 40*a* to generate risk level assignment for a patient based on the derived features from the classifier being applied to healthcare data for the patient.

In some embodiments, a next best actions module 105 employs a trained next best actions model 40*b*. Training of the model 40*b* may include training based on historical healthcare data (e.g., data from patient healthcare database 101 or case management database 102). This data encompasses both structured and unstructured historical healthcare data. As a pivotal part of its training, the system creates a next best actions classifier. To establish this classifier, it identifies key risk features and corresponding thresholds from the historical healthcare patient data. Consequently, the next best actions model 40*b*, once trained, is proficient in generating a comprehensive set of patient next best action recommendations based on these identified features and thresholds. The next best actions module 105 may employ the next best actions model 40*b* to generate patient next best action recommendations for a patient based on the derived features from the classifier being applied to healthcare data for the patient.

In some embodiments, a next best actions module 105 may be trained to identify the next best actions tailored for patients with a specific disease. For example, for patients with ESRD. Such sophisticated training process may involve the creation of a next best actions classifier. The generation of this classifier involves multiple steps. First, by examining the historical healthcare patient data, the system determines the likelihood of a patient being hospitalized due to fluid overload. Subsequently, it evaluates the probability of a patient missing a scheduled hospital appointment. Moreover, in collaboration with the dialysis adequacy criterion, the system discerns the chances of a patient experiencing abnormal dialysis adequacy. The historical healthcare patient data also aids the system in establishing the optimal dry weight of patients as a result of dialysis. Lastly, the system determines any potential changes needed in erythropoiesis-stimulating agents ("ESA") and Iron Supplements ("IS") dosages for the patient. The next best actions classifier encapsulates these determinations, namely, the probabilities related to hospitalization due to fluid overload, missed appointments, abnormal dialysis adequacy, the optimal dry weight due to dialysis, and alterations in ESA or IS dosages. Employing the next best actions classifier, the next best actions module 105 can efficiently generate a comprehensive set of patient next best actions recommendations.

In some embodiments, a disease state transition predictions module 106 employs a trained disease state transition predictions model 40*c*. Training of the model 40*b* may include training based on historical healthcare data. This data encompasses both structured and unstructured historical healthcare data. Central to this training is the crafting of a disease state transition classifier. The formation of this classifier requires the system to analyze the historical healthcare patient data, pinpointing vital disease state features and their respective thresholds. This disease state transition classifier embodies these identified features and thresholds. After completing its training, the disease state transition predictions model 40*c* becomes proficient in producing a prediction related to patient disease state transition, drawing upon the insights gained from the classifier. The disease state transition predictions module 106 may employ the disease state transition predictions model 40*c* to generate disease state transition predictions for a patient based on the derived features from the classifier being applied to healthcare data for the patient.

In some embodiments, an unknown patient identification module 107 employs a trained unknown patient identification model 40*d*. Training of the model 40*d* may include training based on historical healthcare data. This data encompasses both structured and unstructured historical healthcare data. The training uses this data to make a patient identification classifier. This classifier is based on specific patient features and set values, or thresholds. Once trained, the unknown patient identification model 107 can predict if a patient's identification is unknown or not. The unknown patient identification module 107 may employ the unknown patient identification model 40*d* to generate unknown patient identification for a patient based on the derived features from the classifier being applied to healthcare data for the patient.

Figure 2:
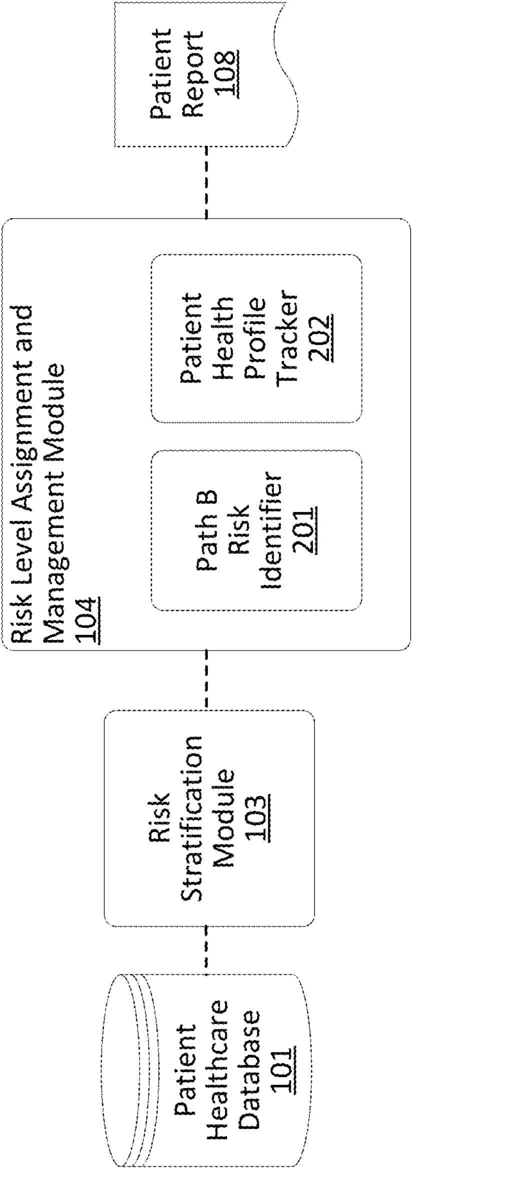
FIG. 2 is a diagram that illustrates a risk stratification module and a risk level assignment and management module in accordance with one or more embodiments.

FIG. 2 is a diagram that illustrates a risk stratification module and risk level assignment and management module in accordance with one or more embodiments. In some embodiments, the risk stratification module 103 obtains data from the patient healthcare database 101 and processes the obtained data to determine a risk stratification assessment, which may, for example, include one or both of a patient stratification score and a binary classification. Following this, the risk level assignment and management module 104 may receive inputs from the risk stratification module 103, which may include, for example, relevant data sourced from the patient healthcare database 101 and also data designated as Path B labeled patient data. The risk level assignment and management module 104 may then process this combined data. Moreover, this module employs two distinct methods: one to ascertain the risk levels for the Path B labeled patient data, and another to determine risk levels for both existing and incoming patients. This may be accomplished by a Path B risk identifier 201 which clusters each data point. Each data point can belong to more than one cluster but with varying degree of probabilities. Based on the probability, it may assign the cluster class such that items in the same cluster that are very similar, while items belonging to different clusters are as dissimilar as possible. The effectiveness of the technique may be based on minimizing the homogeneity within the clusters and separation across the clusters. A patient health profile tracker 202 may then determine the risk levels associated for the patient by tracking the near risk profiles of the patients. This tracking may be accomplished by automatically classifying the patients to their corresponding risk buckets determined by the clustering class. Such processes may serve to treat and manage the chronic disease patient or patients appropriately by devising hyper personalized recommendations that may then be incorporated into the patient report 108.

In some embodiments, a risk level assignment and management module 104 may employ a Path B risk identifier 201 to cluster data with respect to each patient. For example, patients may be allocated to specific clusters based on probability estimates. Those with a low probability designation are perceived as dynamic and adept at transitioning between clusters. From a care management standpoint, such members hold significant interest. Additionally, each cluster may undergo a detailed analysis to pinpoint the most significant attributes and their respective average values. These values serve as distinguishing features for each cluster. Based on these average values, cluster 1 may be categorized as "Low risk," cluster 2 as "Medium risk," and cluster 3 as "High risk."

In some embodiments, a risk level assignment and management module 104 may measure the effectiveness of the clustering using a specific metric. For example, using a FPC metric ("Fuzzy Partitioning Coefficient").

In some embodiments, a risk level assignment and management module 104 may employ a machine learning classifier model. For example, using risk bucket assignments as target labels, a Random Forest classifier model may be trained on Path B members generated by a risk stratification module to predict risk buckets for new as well as existing patients on a new time window.

In some embodiments, a risk level assignment and management module 104 may ingest critical inputs/attributes contributing towards this classification. For example, a patient's dry weight, urea reduction ratio ("URR"), blood urea nitrogen ("BUN") levels, potassium, creatinine levels, etc.

In some embodiments, a risk level assignment and management module 104 may receive patient data from a healthcare database. This data may have both structured and unstructured parts. Using this data (e.g., applying the data to model 40*a*), the risk level assignment and management module makes a risk level assignment for the patient. This involves creating a risk score for the patient, which is based on their stratification score and a binary classification. Depending on the risk score, the patient is then placed into a specific risk category. The output can either stand alone or be integrated into a comprehensive patient report.

Figure 3:
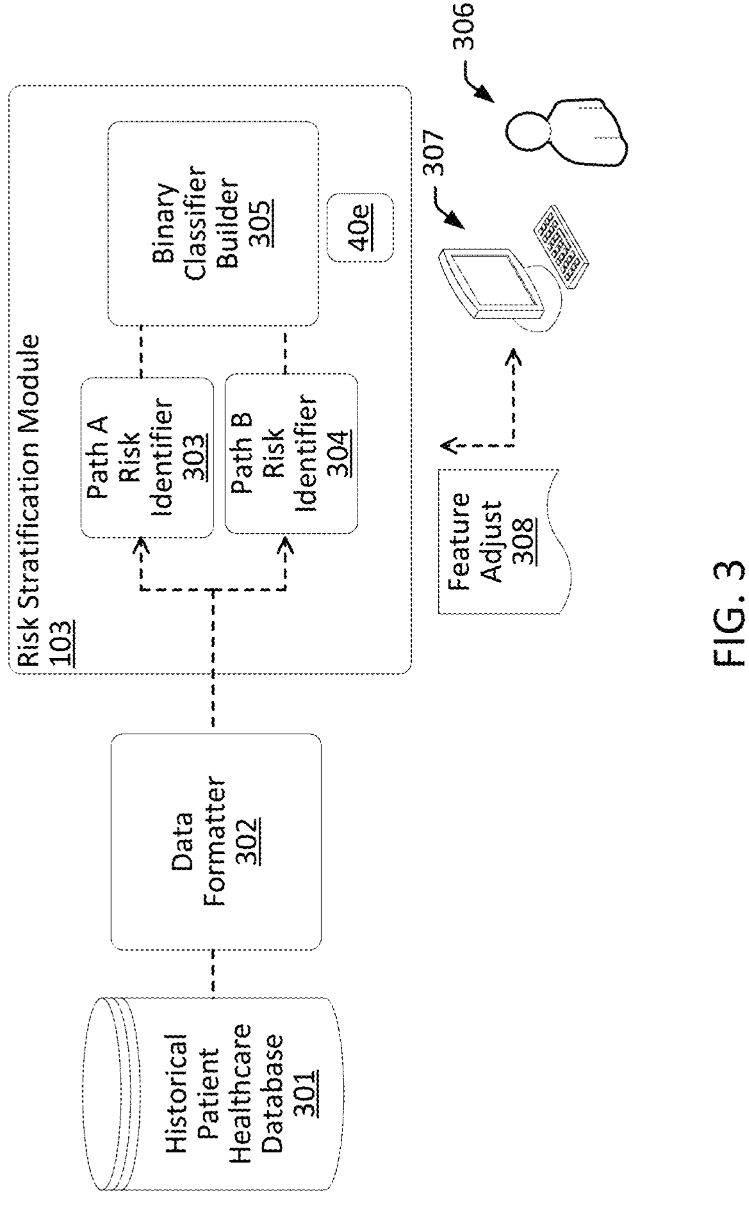
FIG. 3 is a diagram that illustrates a risk stratification module training environment in accordance with one or more embodiments.

FIG. 3 is a diagram that illustrates a risk stratification module training environment 300 in accordance with one or more embodiments. In the illustrated embodiment, a risk stratification model 40*e* employed by the module 103 is trained using a diverse dataset from a historical patient healthcare database 301. For example, the historical patient healthcare database might contain data types such as patient medical histories, laboratory test results, and radiological imaging reports, etc. Before analysis, this data is processed by a data formatter 302, which utilizes a series of structuring algorithms to shape the data for the comprehension of the risk stratification module 103. This formatting stage is crucial, laying the foundation for the risk stratification module 103 to be consistently trained and retrained on data with a similar structure in the future. The formatted data may then be ingested and processed by the risk stratification module 103. The processing may involve employing target labels (Path A vs. Path B) that are determined based on an analysis of hospital billed amounts for a particular range of years. For example, the Path B risk identifier 304 may determine whether a patient is displaying a declining average in billed amounts from such a range are categorized under Path B. Conversely, the Path A risk identifier 303 may determine whether a patient is exhibiting an increasing trend and if so, labels them as Path A. A user 306 has the option to engage directly in the process via a client access point 307, allowing them to communicate with the risk stratification module 103. This interaction facilitates adjustments in features, parameters, and thresholds 308 of the model 40*e*. By doing so, the user can personalize the training of the risk stratification model 40*e* and module 103. This ensures that the model 40*e* and module 103 generate results specifically aligned with select disease parameters or other vital indicators, ultimately aiming for the desired patient stratification score and binary classification. Once all the patient data is categorized, the final step may occur where the Path A and Path B categorized data sets are ingested by the binary classifier builder 305. The binary classifier builder 305 may then build out the desired binary classifier learning from the Path A and Path B categorized dataset and compare against the initial input data. The binary classifier builder 305 may employ numerous machine learning models that are developed and trained based on the path A and path B categorized dataset. The binary classifier builder may then build out the preferred model that is then used to generate the patient stratification score or binary classification for the patient by the risk stratification module 103. Although certain embodiments are described with a binary classifier (e.g., classifying between two states) for the purpose of illustration, embodiments may include classifying between any suitable number of states (e.g., a classifier classifying between three, four or more states).

In some embodiments, a risk stratification module 103 may include a list of inputs that generally comprise of medical claims, prescription claims, provider information, and biologics/labs information. FIG. 9A is a diagram that provides an example list 900*a* of inputs in accordance with one or more embodiments.

In some embodiments, a performance assessment may be conducted among the machine learning models employed among the binary classifier builder 305. This performance assessment may occur using a six-fold cross-validation method. For example, the dataset may be randomly divided into six segments, with training conducted on five segments and testing on one. This process may be repeated multiple times with different random splits, and the results are averaged across all iterations. To further facilitate this, a user 306 may intervene via a client access point 307, to establish a set of uniform training controller objects, maintaining consistent train/test divisions and model evaluation metrics, which may be employed repeatedly. An accuracy metric may be used to evaluate the model's performance on the test/validation data. For example, the accuracy metric may be a percentage of the number of correctly predicted instances.

In some embodiments, a risk stratification module may employ a specific machine learning algorithm to capture the underlying data patterns in the training dataset. The machine learning algorithms may include a Logistic Regression, Decision Trees, Support Vector Machines, Random Forest, or XGBoost. For example, a Random Forest algorithm may produce many small classification trees on random fractions of the data until a voting mechanism is triggered. The voting mechanism subsequently orders and deduces the importance of the predictive variables. For example, approximately 2000 decision trees may be employed to make the predictions, with a majority vote (for Path A vs Path B classification). Each tree in the forest may be built on a fraction ("in bag") of the data (the fraction that may have been used for training the algorithm), and for each individual of the remaining fraction ("out of bag" or "OOB"), the tree predicts a class. The goal is to obtain the smallest possible OOB estimate error. The OOB error is a measure of the random forest prediction error and, thus is indicative of the model's overall performance.

In some embodiments, the OOB error with respect to a model employing a machine learning algorithm may include a set of parameters. For example, a default set of parameters may be utilized and then a set of hyper-parameters may be employed in order to further tune the model. FIG. 9B is a diagram that illustrates an example default set of parameters 900*b* in accordance with one or more embodiments.

Tuning hyperparameters may be done to achieve two goals: (1) increase the predictive power of the model and (2) improve its speed. To assess the performance of a model, training and validation accuracies may have to be computed via metrics. For example, "Accuracy" may be one of the metrics for evaluating classification models. Accuracy may be defined as the following equation:

$$\text{Accuracy}=(TP+TN)/(TP+TN+FP+FN)$$

The variables may be set out as follows: TP=true positive, FP=false positive, FN=false negative, and TN=true negative. A TP may be a result where the model correctly predicts the positive class. Similarly, a TN may be a result where the model correctly predicts the negative class. A FP may be a result where the model incorrectly predicts the positive class. A FN may be a result where the model incorrectly predicts the negative class. The modeling methodology, which involves utilizing parameters and other hyperparameters for tuning, testing, and prediction, can be applied to any module discussed herein.

In some embodiments, a model's binary classifier builder may identify a particular feature's significance within an optimal model. For example, a model may employ a mean decrease Gini index. Conversely, a higher value of this metric signifies greater importance of the variable in the model, as it quantifies the reduction in the Gini index when the feature is excluded. For example, treatment types, coverage, demographics of the patients and their dry weights may play an important role in determining the health trajectory of the patients and this information plays a crucial role in managing the health journey of ESRD patients. Notably, techniques described here are capable of providing a highly efficient and accurate mechanism for identification of conditions. For example, validations have shown models employing the described techniques achieve over 93% accuracy in identifying patient trends for ESRD, with an accuracy over at or above approximately 69% for many other conditions, including Cardio, Diabetes and pre-diabetes, and mental health.

Figure 4:
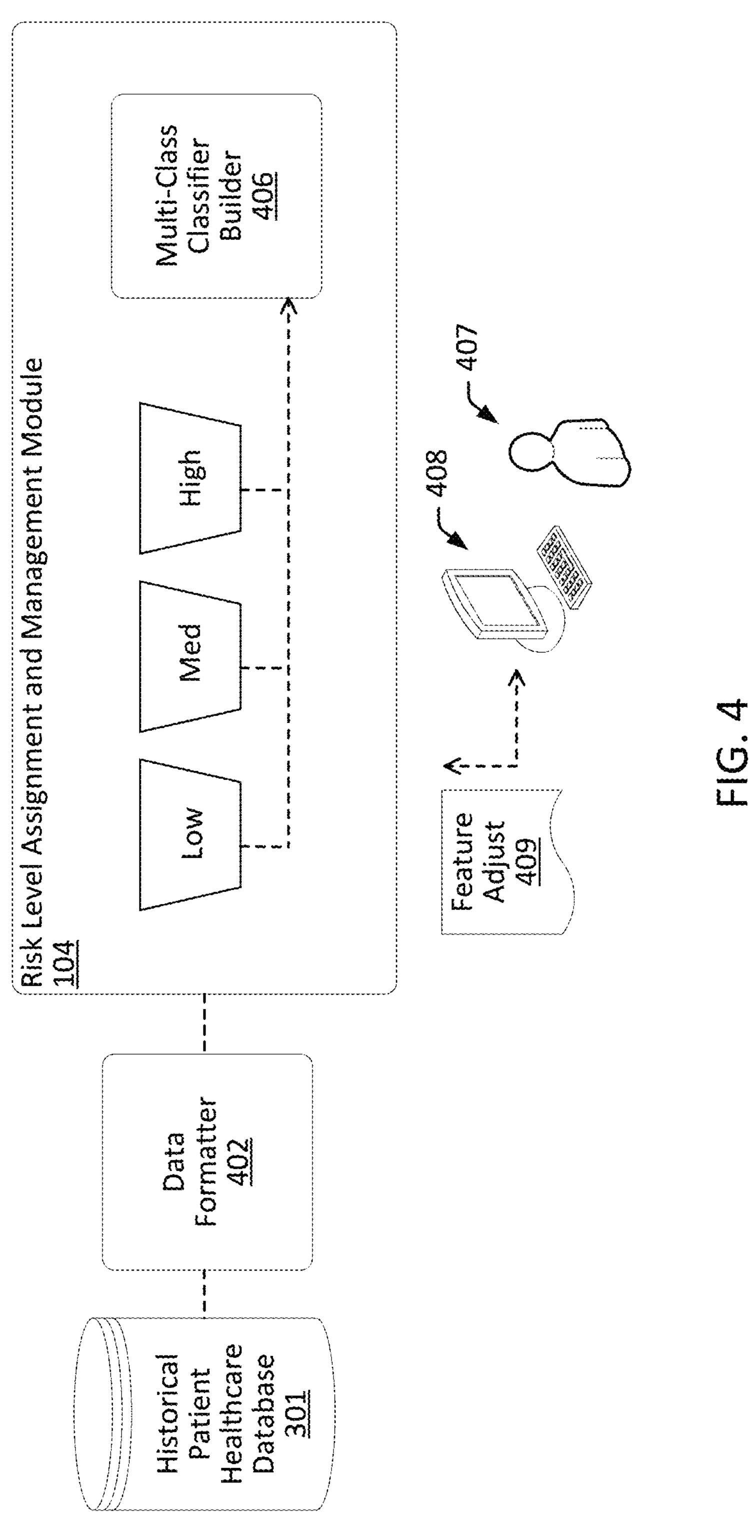
FIG. 4 is a is a diagram that illustrates a risk level assignment and management module training environment in accordance with one or more embodiments.

FIG. 4 is a is a diagram that illustrates a risk level assignment and management module training environment 400 in accordance with one or more embodiments. In the illustrated embodiment, the risk level assignment and management module 104 may be trained upon an array of data from an historical patient healthcare database 301. A data formatter 402 may first massage the data and tailor its format to appropriately be ingested by the risk level assignment and management module 104. The risk level assignment and management module 104 may then employ a series of risk classifiers for low, medium, or high-risk to categorize the data based on key features indicative of patient risk. A user 407 may similarly intervene by adjusting key features 409 using a client access point 408. Once the patient is categorized based on low, medium, or high-risk classifications, the multi-class classifier builder 406 may then build out the preferred model that is then used to generate risk level scoring of the patient by the risk level assignment and management module 104.

Figure 5:
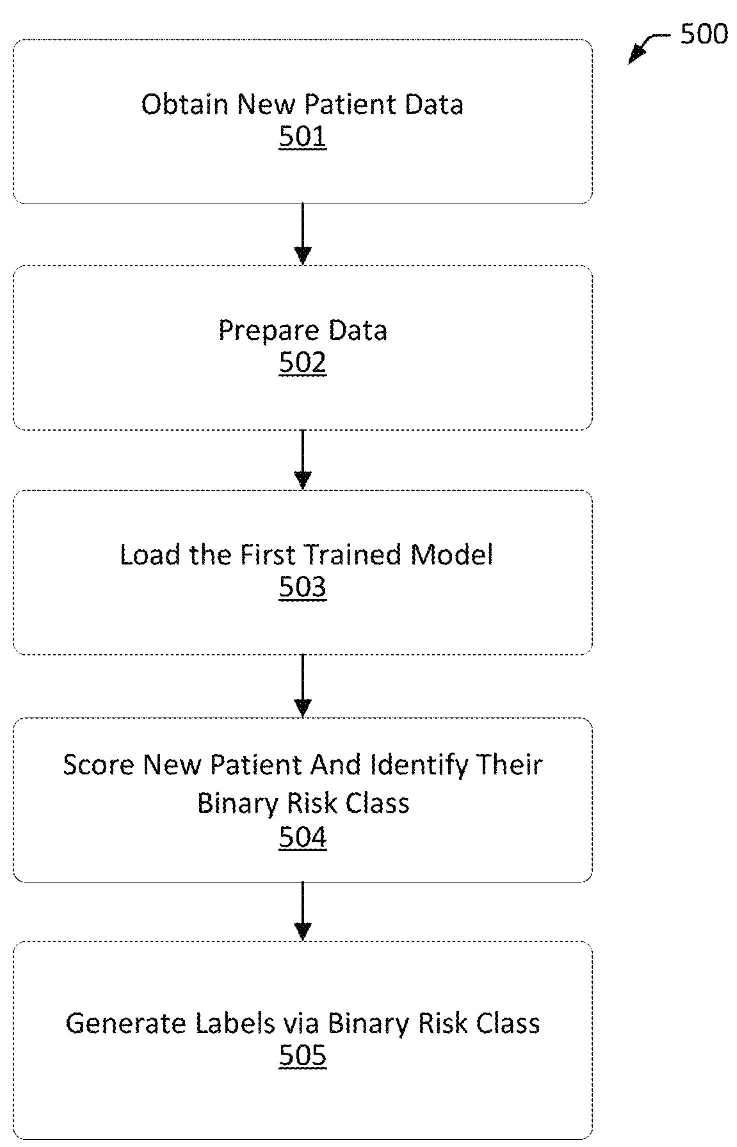
FIG. 5 is a diagram that illustrates a method for generating a patient's risk stratification profile using a risk stratification module in accordance with one or more embodiments.

FIG. 5 is a flowchart diagram that illustrates an inferential sequence for generating a patient's risk stratification profile using the risk stratification module 103 in accordance with one or more embodiments. In the illustrated embodiment, the risk stratification module 103 may obtain new patient data (block 501) to be processed and may output a risk stratification assessment that includes a patient stratification score and a binary classification for the patient. The new patient data (block 501) may first be prepared (block 502) to conform to the proper format that is ingestible by the risk stratification module 103. After the formatted data is ready to be ingested, the risk stratification module 103 may load the first trained model (block 503). The first trained model (block 503) may then ingest and process the data to generate the new patient score and identify their binary risk class (block 504). Afterwards, the risk stratification module 103 may generate labels via the patient's binary risk class (block 505).

In some embodiments, patient data is received from a healthcare database. The data may be made up of both organized (structured) and less organized (unstructured) healthcare information. Using this data, a determination engine (e.g., an associated model 40) makes predictions about the patient's disease state and how it might change. To make these predictions, the engine calculates transition probabilities for the patient based on their data. The output can either stand alone or be integrated into a comprehensive patient report.

In some embodiments, the medical management framework may also consist of a module that can identify the transition probabilities of early-stage CKD patients (stages 1-3) as well as those who have a propensity to move across the stages. Such a framework may consist of trained AI models for every stage of CKD that provide the probabilities of patients to move to the next stage of CKD as well as towards stage 5/6 (also known as ESRD). Based on these predictions, one can identify the patients who require immediate attention, etc. Identifying and treating such patients appropriately could increase their life expectancy and, in some cases, may afford a vital opportunity to reverse disease progression.

In some embodiments, a module may determine the likelihood of early-stage CKD patients (specifically stages 1-3) progressing between stages or those who are prone to shift from one stage to another using inputs/attributes that are indicative of such estimation. FIG. 9C is a diagram that provides an example list 900*c* of data attributes for a module in accordance with one or more embodiments.

In some embodiments, a module may determine the likelihood of early-stage CKD patients (specifically stages 1-3) progressing between stages or those who are prone to shift from one stage to another using target labels and a training data set. For example, target labels may include "YES" for patients transitioning to the next stage and "NO" for non-transitioning patients, which are custom created by analyzing the history of patients (for example, based on ICD10 codes). The training data may also be aggregated at the patient level. Thus, every patient may have one single record for the specified period (where the numerical columns are aggregated, and the categorical columns are counted).

In some embodiments, a module may determine the likelihood of early-stage CKD patients (specifically stages 1-3) progressing between stages or those who are prone to shift from one stage to another using machine learning algorithms that are built and trained against the training dataset. The machine learning algorithms may include a Logistic Regression, Decision Trees, Support Vector Machines, Random Forest, or XGBoost. For example, using "YES" or "NO" as target labels, a Random Forest classifier algorithm may ingest the patient data to predict a disease state transition probability (e.g., from N181 to N182).

In some embodiments, patient data is received from a healthcare database. The data may be made up of both organized (structured) and less organized (unstructured) healthcare information. The determination engine (e.g., a corresponding model 40) uses this data to make predictions about whether a patient's identification is unknown. It does this by calculating a disease propensity score for the patient using their data. The output can either stand alone or be integrated into a comprehensive patient report.

In some embodiments, a module may be able to identify the propensity of patients who are prone towards CKD (even if not currently diagnosed with any of the CKD stages or symptoms). Identifying and treating those patients appropriately at very early stages may help in devising personalized treatment plans and strategies to slow down and/or reverse the disease condition.

Figures 6, 7:
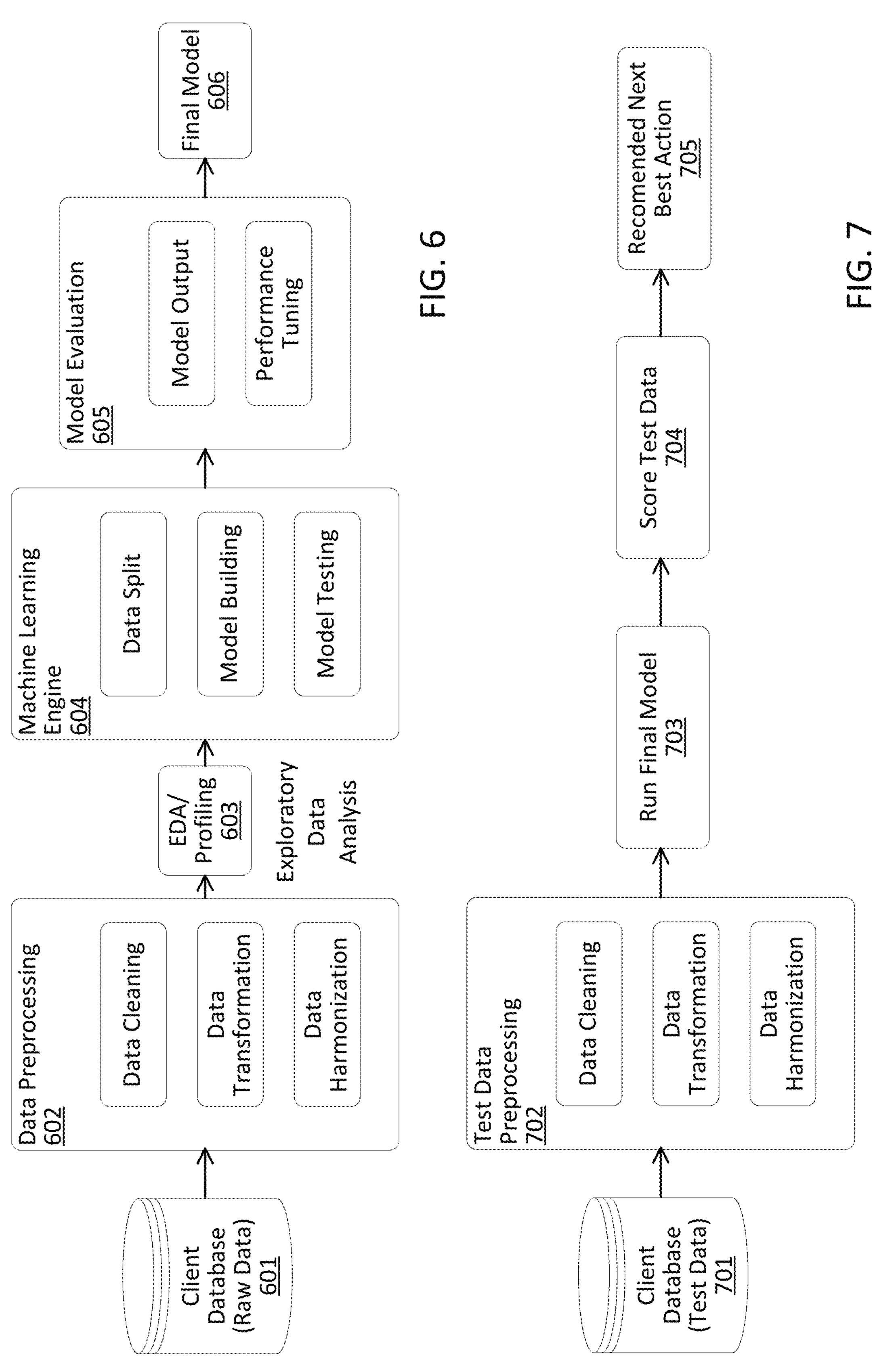
FIG. 6 is a diagram that illustrates a training environment in accordance with one or more embodiments.
FIG. 7 is a diagram that illustrates an inferential sequence for generating a set of patient next best actions using a next best actions module in accordance with one or more embodiments.

FIG. 6 is a diagram that illustrates a training environment that can be applied to train modules in accordance with one or more embodiments. In the illustrated embodiment, a client database 601 may feed the model with raw training data. The raw data may include structured, unstructured, or semi-structured data from multiple sources that have been extracted (this may include both on-prem as well as cloud data sources). The raw training data may first be pre-processed (block 602) where the raw training data is cleaned, transformed, and harmonized to be properly formatted for ingestion by the model. This pre-process transformation and harmonization step may aggregate the raw training data at the patient level, permitting every patient to have one single record for the specified period where the number of claims, billed amounts, etc. have all been aggregated. Afterwards, an Exploratory Data Analysis ("EDA") may perform a patient profiling analysis on the data (block 603). For example, this may include a standard EDA process where the quality of the data is assessed and includes the identification of the outliers, missing values, distribution (skewness/kurtoses), ranges, number of categories (of categoric columns) of the data etc. Subsequently, the machine learning engine 604 generates the preferred model based on the processed training data. The data may then be split into 6 parts, where it is trained on five and tested on one and repeated this several times by changing the random splitting. The model is then built and continuously tested based on the test/validation data. After the model is built out and reaches a first accuracy metric, the model is fine-tuned based on its performance using a second accuracy metric to continuously evaluate the performance of the model on the test/validation data (block 605). Once the second accuracy metric is reached, the final model (block 606) is generated and configured for use.

FIG. 7 is a diagram that illustrates a testing sequence for generating a set of patient next best actions using next best actions module 105 in accordance with one or more embodiments. In the illustrated embodiment, a client database 701 may feed the model with test data. The test data may first be pre-processed (block 702) where the test data is cleaned, transformed, and harmonized to be properly formatted for ingestion by the model. Once the data is ready, the final model (block 703) processes the data similar to its ordinary inferential sequence. The processed test data may then be scored (block 704) to determine whether an accuracy score for the final model is met. If the accuracy score is met, the output can be utilized to recommend next best actions for patients (block 705).

In some embodiments, the patient data is collected from a healthcare database, which has both organized (structured) and less organized (unstructured) information. Using this data, a determination engine (e.g., a corresponding model 40) predicts what might happen next for the patient (patient outcome prediction). Then, based on these predictions, it may suggest a set of recommended next steps or actions for the patient. The output can either stand alone or be integrated into a comprehensive patient report.

In some embodiments, a determination engine (e.g., a corresponding model 40) is trained to suggest the best next steps for patients with ESRD. It uses a next best actions classifier that looks at past patient data. This tool considers several things: the chance a patient might be hospitalized because they have too much fluid, the chance they might miss a hospital appointment, if their dialysis is working properly, their ideal weight after dialysis, and if there's a need to change their ESA or IS medicine doses. The engine uses this tool to recommend the best actions for the patient. The output can either stand alone or be integrated into a comprehensive patient report.

In some embodiments, a module may preemptively identify patients who have higher chances of hospitalization due to the fluid overload. For example, the AI based system may automatically flag patients who show a hospitalization tendency based on their current data attributes. FIG. 9D is a diagram that provides an example list 900*d* of data inputs/attributes for hospitalization prediction in accordance with one or more embodiments.

In some embodiments, a module may preemptively identify patients who have higher chances of hospitalization due to the fluid overload by using target labels and a training data set. For example, labels such as "YES" for hospitalized and "NO" for no-hospitalized may be custom created by analyzing previous hospitalization histories of patients from the training data set. For the "YES" class, the training data may be aggregated (for instance, an average of 3 months prior data from the date of first observed hospitalization within a year) at the patient level. For the "NO" class, the training data set may be aggregated (for instance, an average of 3 months where hospitalization was not recorded within this period of two years) at the patient level as well. Thus, every patient may have one single record for the specified period (where the numerical columns are aggregated, and the categorical columns are counted).

In some embodiments, a module may preemptively identify patients who have higher chances of hospitalization due to the fluid overload by employing various machine learning models. For example, using "Yes" or "No" target labels, a Random Forest classifier model may be trained on various patients to predict the probability of hospitalization of dialysis patients due to fluid overload. Further, the critical attributes may be comprised of treatment types, blood pressure and the observed differences in body temperature and weight within the 2 weeks duration.

In some embodiments, a module may generate a patient no-show prediction, the percentage of missingness of scheduled hospital appointments at the individual patient level. Hospital appointment no-shows is a major issue for healthcare centers since they are quite costly and disruptive. Reducing uncancelled missed appointments can have a tremendous impact on improving efficiency, reducing costs, and improving patient outcomes.

In some embodiments, a module may estimate patient miss percentage using a series of inputs/attributes that are indicative of such estimation. FIG. 9E is a diagram that provides an example list 900*e* of data inputs/attributes in accordance with one or more embodiments.

In some embodiments, a module may use a list of attributes as predictor values to generate a patient no-show prediction. For example, while creating target labels, a model may extract and analyze historical data corresponding to a missing/no-show category. This data may further be separated into six different "no-shows" buckets, each corresponding to a different no-show percentage. Essentially, this may estimate the percentage of no-shows for each patient. Further, based on the computed percentage, each patient may be assigned to a corresponding no-show percentage bucket. For example, "Bucket 0" may contain all the patients whose no-show percentage is <10%; "Bucket 1" may contain all patients whose no-show percentage is between 10-20%; "Bucket 2" may contain all the patients whose no-show percentage is between 20-30%; "Bucket 3" may contain all the patients whose no-show percentage is between 30-40%; "Bucket 4" may contain all the patients whose no-show percentage is between 40-50%; and "Bucket 5" may contain all the patients whose no-show percentage is >=50%. Each no-show bucket may be used as target labels and based on the prediction of the target label. Consequently, the patient no-show prediction can then be determined.

In some embodiments, a module may generate a patient no-show prediction by employing a machine learning model that is built and trained against a training dataset. The machine learning algorithms may include a Logistic Regression, Decision Trees, Support Vector Machines, Random Forest, or XGBoost. For example, using a bucket classification as target labels, a multi-class Random Forest classifier algorithm may be trained on patient data to predict the percentage of no-shows.

In some embodiments, a module may identify patients who are indicating abnormal dialysis adequacy measures. For example, if a patient is indicating a Urea Reduction Ratio ("URR") of less than 65% and Clearance test ("KT/V") or less than 1.2, the module may automatically flag the patient to have an abnormal adequacy measure.

In some embodiments, a module may identify patients who are indicating abnormal dialysis adequacy measures using a series of inputs/attributes that are indicative of such identification. FIG. 9F is a diagram that provides an example list 900*f* of data inputs/attributes in accordance with one or more embodiments.

In some embodiments, a module may identify patients who are indicating abnormal dialysis adequacy measures using target labels and a training data set. For example, "YES" may indicate adequate levels (URR>=65% and KT/V>=1.2) and "NO" may indicate non-adequate levels (URR<65% and KT/V<1.2), which may be custom created (for both models) by analyzing previous historical measures of URR and KT/V. For both the URR and KT/V models, the training data may be aggregated over one year of data at the patient level. Thus, every patient may have one single record for the specified period (where the numerical columns were aggregated, and the categorical columns were counted).

In some embodiments, a module may identify patients who are indicating abnormal dialysis adequacy measures using machine learning models that are built and trained against a training dataset. For example, using "YES" or "NO" as target labels as well as two separate Random Forest classifier algorithms (URR model and KT/V model) that may be trained on patient data to predict an adequate dialysis measure.

In some embodiments, a module may automatically predict the direction of a patient's dry weight where it will either increase, decrease, or hold in comparison to a previous measurement. Knowledge of the proper dry weight plays a critical role in the efficiency of dialysis and the survival of hemodialysis patients.

In some embodiments, a module may automatically predict the direction of a patient's dry weight using a series of inputs/attributes that are indicative of such prediction. FIG. 9G is a diagram that provides an example list 900*g* of data inputs/attributes in accordance with one or more embodiments.

In some embodiments, a module may automatically predict the direction of a patient's dry weight using target labels and a training data set. For example, the target labels may include "Increase," "Decrease," and "Hold," which are custom created by analyzing the previous dry weight measure of patients. The training data may be aggregated over two years of data at the patient level. Thus, every patient may have one single record for the specified period (where the numerical columns are aggregated, and the categorical columns are counted).

In some embodiments, a module may automatically predict the direction of a patient's dry weight using machine learning models that are built and trained against the training dataset. For example, using "Increase," "Decrease," or "Hold" as target labels, a Random Forest classifier algorithm may be trained on patient data to predict the direction of the dry weight estimate for the next visit.

In some embodiments, a module may predict optimal ESA and IS dosages (at least qualitatively) that are geared toward the effective treatment of anemia in dialysis patients. Further, the module may automatically flag and determine whether patient's ESA or IS dosages should be increased, decreased, or held.

In some embodiments, a module may predict optimal ESA and IS dosages using a series of inputs/attributes that are indicative of such prediction. FIG. 9H is a diagram that provides an example list 900*h* of data inputs/attributes in accordance with one or more embodiments.

In some embodiments, a module may predict optimal ESA and IS dosages using a training data set and target labels. For example, target labels may include "Increase ESAs," "Decrease ESAs," or "Hold ESAs" and "Increase ISs" or "Hold ISs," which may be custom created by analyzing the previous historical measures of ESAs and ISs dosages. Training data has been aggregated over one year of data at the patient level. Thus, every patient may have one single record for the specified period (where the numerical columns are aggregated, and the categorical columns are counted).

In some embodiments, two separate modules may predict optimal ESA and IS dosages. For example, two separate models may be built for ESA estimates as well as IS estimates.

In some embodiments, a module may predict optimal ESA and IS dosages using machine learning models that are built and trained against the training dataset. For example, using "Increase ESAs," "Decrease ESAs," or "Hold ESAs" and "Increase ISs" or "Hold ISs" as target labels, two separate Random Forest classifier algorithms (one for the ESA model and another for the IS model) may be trained on patient data to predict the qualitative direction of the ESA and IS dosages.

In some embodiments, a module may recommend approximately 20+ generic NBAs which are categorized into clinical, treatment & prescriptions, care plans, behavioral, and educational & outreach, etc. For example, the clinical recommendations may be based on the specific lab results along with the pre-determined acceptable thresholds for a specific lab test. These tests may also be ranked among multiple lab tests. For example, the treatment & prescriptions category may include recommendations about the most suitable providers within and out of network, ER visits, dialysis frequency, prescription refills and frequency of refills, drug adherence etc. For example, the care plans category may recommend the best care plan suitable for a patient. This care plan may be premised upon a patient's current state of health, dialysis center recommendation, etc. For example, the behavioral category may suggest life-style recommendations, prescribed exercises, etc. Lastly, for example, the educational and outreach category may identify the best way of contacting patients as well as the likelihood that patients way the patients would respond and recommend various measures of communication.

Figure 8:
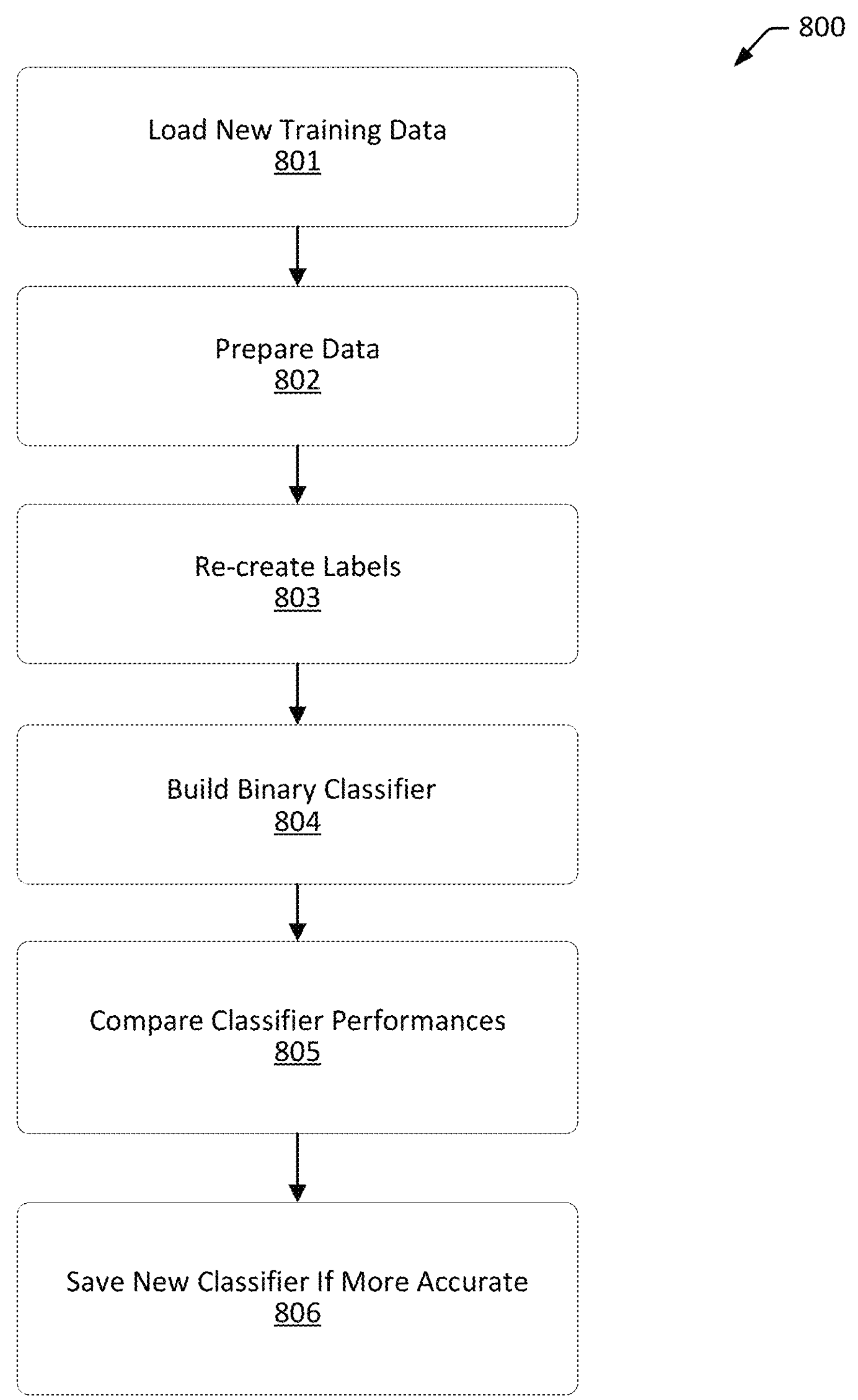
FIG. 8 is a diagram that illustrates a re-training sequence applicable for refining and updating a risk stratification module in accordance with one or more embodiments.

FIG. 8 is a diagram that illustrates a retraining sequence that can be applied to re-train the risk stratification module in accordance with one or more embodiments. In the illustrated embodiment, new training data may be loaded into the system (block 801) for the risk stratification module 103 to ingest. The collection of new training data may include a step where for every three months, the previous six months of data is aggregated (for new patients and for old patients, the existing data may be left as is) and added to the previous training data set. The data may then be prepared (block 802) to conform to the proper format that is ingestible by the risk stratification module 103. Next, labels may be re-created similar to the module's first training instance and configured to be applied to the new training data. The new categorized patient data may then be ingested to build out the binary classifier builder (block 804). The binary classifier builder (block 804) may then build out the desired binary classifier learning from the newly categorized training data. Similar to the inferential step, the binary classifier builder (block 804) may employ numerous machine learning models that are developed and trained based on the categorized dataset to build out the preferred re-trained binary risk classifier. The preferred re-trained binary risk classifier may then be compared against the prior preferred binary risk classifier (block 805). The comparison may include generating an accuracy score among each classifier and determining which score is higher. If the preferred re-trained binary risk classifier has a higher accuracy score than the prior preferred binary risk classifier, then the prior preferred model is overwritten by the preferred re-trained binary risk classifier (block 806). If not, the prior preferred binary risk classifier remains in place and continues to perform inferential steps for the risk stratification module 103.

All these modules can be utilized in conjunction with other modules or can be utilized as stand-alone modules. In addition to the embodiments throughout this application, these core modules among the medical management framework environment are flexible. Hence, several variants of the medical management framework may be configured to assess specific disease states and can be designed to suggest certain actions based on a patient diagnosis. For example, the medical management framework may be fine-tuned towards the treatments of kidney failure, heart failure, diabetes, prediabetes, mental health, COPD etc.

Figure 10:
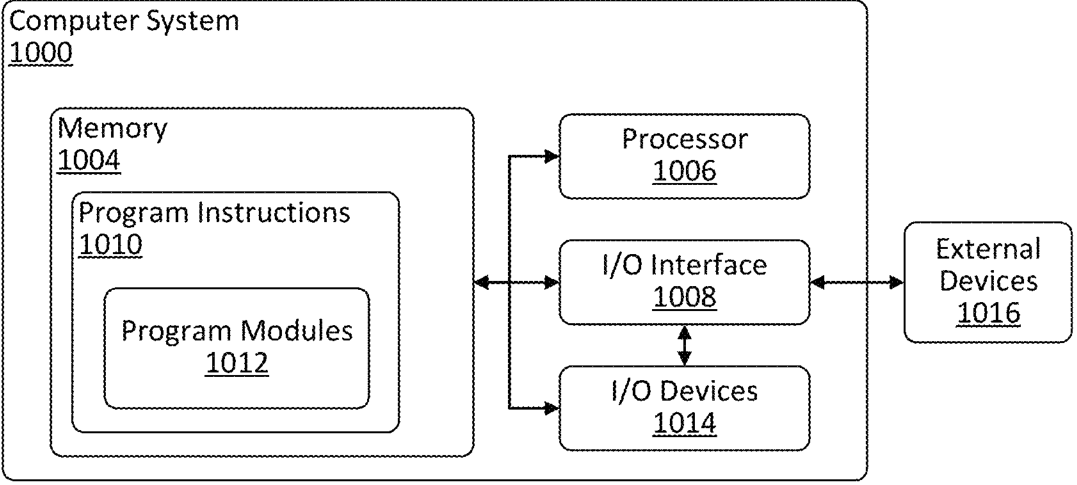
FIG. 10 is a diagram that illustrates an example computer system in accordance with one or more embodiments.

FIG. 10 is a diagram that illustrates an example computer system (or "system") 1000 in accordance with one or more embodiments. The system 1000 may include a memory 1004, a processor 1006 and an input/output (I/O) interface 1008. The memory 1004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), or bulk storage memory (e.g., CD-ROM or DVD-ROM, hard drives). The memory 1004 may include a non-transitory computer-readable storage medium having program instructions 1010 stored on the medium. The program instructions 1010 may include program modules 1012 that are executable by a computer processor (e.g., a processor of system 22) to cause the functional operations described, such as those described with regard to the entities described (e.g., healthcare monitoring system 22, healthcare data providers 24, and healthcare providers 26, and associated modules and elements thereof), or some or all of method 500 or 800.

The processor 1006 may be any suitable processor capable of executing program instructions. The processor 1006 may include one or more processors that carry out program instructions (e.g., the program instructions of the program modules 1012) to perform the arithmetical, logical, or input/output operations described. The processor 1006 may include multiple processors that can be grouped into one or more processing cores that each include a group of one or more processors that are used for executing the processing described here, such as the independent parallel processing of partitions (or "sectors") by different processing cores to generate a simulation of a reservoir. The I/O interface 1008 may provide an interface for communication with one or more I/O devices 1014, such as a joystick, a computer mouse, a keyboard, or a display screen (e.g., an electronic display for displaying a graphical user interface (GUI)). The I/O devices 1014 may include one or more of the user input devices. The I/O devices 1014 may be connected to the I/O interface 1008 by way of a wired connection (e.g., an Industrial Ethernet connection) or a wireless connection (e.g., a Wi-Fi connection). The I/O interface 1008 may provide an interface for communication with one or more external devices 1016, computer systems, servers or electronic communication networks. In some embodiments, the I/O interface 1008 includes an antenna or a transceiver.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims. Headings used here are for organizational purposes only and are not meant to be used to limit the scope of the description.

It will be appreciated that the processes and methods described here are example embodiments of processes and methods that may be employed in accordance with the techniques described here. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination thereof. Some or all of the portions of the processes and methods may be implemented by one or more of the processors/modules/applications described here.

As used throughout this application, the word "may" is used in a permissive sense (meaning having the potential to), rather than the mandatory sense (meaning must). The words "include," "including," and "includes" mean including, but not limited to. As used throughout this application, the singular forms "a," "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A method comprising:
   receiving, by a computer system from a healthcare database, patient data, the patient data comprising structured healthcare data and unstructured healthcare data;
   generating, by a first determination engine based on the patient data, a patient risk stratification, the generating of the patient risk stratification comprising:
      generating stratification scoring of the patient based on the patient data; and
      determining, based on the stratification scoring of the patient, a binary classification for the patient;
   generating, by a second determination engine based on the patient data, a patient risk level assignment, the generating of the patient risk level assignment comprising:
      generating risk level scoring of the patient based on the stratification scoring of the patient and the binary classification for the patient; and
      determining, based on the risk level scoring of the patient, a risk category for the patient;
   generating, by a third determination engine based on the patient data, a set of patient next best actions, the generating of the set of patient next best actions comprising:
      determining, based on the patient data, a patient outcome prediction; and
      generating, based on the predictions of patient outcomes, the set of patient next best actions;
   generating, by a fourth determination engine, a patient disease state transition prediction, the generating of the patient disease state transition prediction comprising:
      determining, based on the patient data, a set of transition probabilities for the patient;
   generating, by a fifth determination engine, a patient unknown identification prediction, the generating of the patient unknown identification prediction comprising:
      determining, based on the patient data, a disease propensity score for the patient; and
   generating, by a sixth determination engine based on the patient risk stratification, patent risk level assignment, patient next best actions, patient disease state transition predictions, and patient unknown identification predictions, a patient diagnosis report.
2. The method of embodiment 1, wherein the first determination engine comprises a risk stratification model, and the method further comprising training the risk stratification model, comprising:
   receiving, by the computer system, historical patient data, the historical patient data comprising structured historical healthcare data and unstructured historical healthcare data;
   generating a binary risk classifier comprising determining, based on the historical patient healthcare data, key risk features and thresholds, wherein the binary risk classifier comprises the key risk features and thresholds, and
   wherein the risk stratification model is trained to generate the patient risk stratification based on the binary risk classifier.
3. The method of embodiment 2, further comprising re-training the risk stratification model, comprising:
   receiving, by a computer system, updated historical patient data, the updated historical patient data comprising updated structured historical healthcare data and unstructured historical healthcare data;
   generating an updated binary risk classifier comprising determining, based on the updated historical patient healthcare data, key risk features and thresholds, wherein the binary risk classifier comprises the key risk features and thresholds;
   generating an accuracy score of the updated binary risk classifier and the binary risk classifier;
   determining, based on comparing the accuracy score of the updated binary risk classifier with the accuracy score of the binary risk classifier, that the updated risk classifier is more accurate than the binary risk classifier; and
   overwriting the binary risk classifier with the updated risk classifier in response to determining that the updated binary risk classifier is more accurate than the binary risk classifier,
   wherein the risk stratification model is re-trained to generate the patient risk stratification based on the updated binary risk classifier.
4. The method of any one of embodiments 1-3, wherein the second determination engine comprises a risk level assignment model, and the method further comprising training the risk level assignment model, comprising:
   receiving, by the computer system, historical patient data, the historical patient data comprising structured historical healthcare data and unstructured historical healthcare data;
   generating a multi-class risk level classifier comprising determining, based on the historical healthcare patient data and the binary classification of the patient, key risk features, wherein the multi-class risk level classifier comprises the key risk features; and
   wherein the risk level assignment model is trained to generate the patient risk level assignment based on the multi-class risk level classifier.
5. The method of embodiment 4, further comprising re-training the risk level assignment model, comprising:
   receiving, by a computer system, updated historical patient data, the updated historical patient data comprising updated structured historical healthcare data and unstructured historical healthcare data;
   generating an updated multi-class risk level classifier comprising determining, based on the updated historical patient healthcare data and the binary classification of the patient, key risk features, wherein the multi-class risk level classifier comprises the key risk features;
   generating an accuracy score of the updated multi-class risk level classifier and the multi-class risk level classifier;
   determining, based on comparing the accuracy score of the updated multi-class risk level classifier with the accuracy score of the multi-class risk level classifier, that the updated multi-class risk level classifier is more accurate than the multi-class risk level risk classifier; and
   overwriting the multi-class risk level classifier with the updated multi-class risk level classifier in response to determining that the updated multi-class risk level classifier is more accurate than the multi-class risk level risk classifier, wherein the risk level assignment model is re-trained to generate the patient risk level assignment based on the updated multi-class risk level classifier.

6. The method of any one of embodiments 1-5, wherein the third determination engine comprises a next best actions model, and the method further comprising training the next best actions model, comprising:
receiving, by the computer system, historical patient data, the historical patient data comprising structured historical healthcare data and unstructured historical healthcare data;
generating a next best actions classifier comprising determining, based on the historical healthcare patient data, key risk features and thresholds, wherein the next best actions classifier comprises the key risk features and thresholds; and
wherein the next best actions model is trained to generate the set of patient next best actions based on the next best actions classifier.

7. The method of embodiment 6, further comprising re-training the next best actions model, comprising:
receiving, by a computer system, updated historical patient data, the updated historical patient data comprising updated structured historical healthcare data and unstructured historical healthcare data;
generating an updated next best actions classifier comprising determining, based on the updated historical patient healthcare data, key risk features and thresholds, wherein the next best actions classifier comprises the key risk features and thresholds;
generating an accuracy score of the updated next best actions classifier and the next best actions classifier;
determining, based on comparing the accuracy score of the updated next best actions classifier with the accuracy score of the next best actions classifier, that the next best actions classifier is more accurate than the next best actions classifier; and
overwriting the next best actions classifier with the updated next best actions classifier in response to determining that the updated next best actions classifier is more accurate than the next best actions classifier,
wherein the next best actions model is re-trained to generate the set of patient next best actions based on the updated next best actions classifier.

8. The method of any one of embodiments 1-7, wherein the fourth determination engine comprises a disease state transition prediction model, and the method further comprising training the disease state transition prediction model, comprising:
receiving, by the computer system from, historical patient data, the historical patient data comprising structured historical healthcare data and unstructured historical healthcare data;
generating a disease state transition classifier comprising determining, based on the historical healthcare patient data, key disease state features and thresholds, wherein the disease state transition classifier comprises the key disease state features and thresholds; and
wherein the disease state transition prediction model is trained to generate the patient disease state transition prediction based on the disease state transition classifier.

9. The method of embodiment 8, further comprising re-training the disease state transition prediction model, comprising:
receiving, by a computer system, updated historical patient data, the updated historical patient data comprising updated structured historical healthcare data and unstructured historical healthcare data;
generating an updated disease state transition classifier comprising determining, based on the updated historical patient healthcare data, key disease state features and thresholds, wherein the disease state transition classifier comprises the key disease state features and thresholds;
generating an accuracy score of the updated disease state transition classifier and the disease state transition classifier;
determining, based on comparing the accuracy score of the updated disease state transition classifier with the accuracy score of the disease state transition classifier, that the disease state transition classifier is more accurate than the disease state transition classifier; and
overwriting the disease state transition classifier with the updated disease state transition classifier in response to determining that the updated disease state transition classifier is more accurate than the disease state transition classifier,
wherein the disease state transition prediction model is re-trained to the patient disease state transition prediction based on the updated disease state transition classifier.

10. The method of any one of embodiments 1-9, wherein the fifth determination engine comprises an unknown patient identification prediction model, and the method further comprising training the unknown patient identification prediction model, comprising:
receiving, by the computer system, historical patient data, the historical patient data comprising structured historical healthcare data and unstructured historical healthcare data;
generating a patient identification classifier comprising determining, based on the historical healthcare patient data, key patient features and thresholds, wherein the patient identification classifier comprises the key patient features and thresholds; and
wherein the unknown patient identification prediction model is trained to generate the patient unknown identification prediction based on the patient identification classifier.

11. The method of embodiment 10, further comprising re-training the patient unknown identification prediction, comprising:
receiving, by a computer system, updated historical patient data, the updated historical patient data comprising updated structured historical healthcare data and unstructured historical healthcare data;
generating an updated patient identification classifier comprising determining, based on the updated historical patient healthcare data, key patient features and thresholds, wherein the patient identification classifier comprises the key patient features and thresholds;
generating an accuracy score of the updated patient identification classifier and the patient identification classifier;
determining, based on comparing the accuracy score of the updated n patient identification classifier with the accuracy score of the patient identification classifier, that the patient identification classifier is more accurate than the patient identification classifier; and overwriting the patient identification classifier with the updated patient identification classifier in response to determining that the updated patient identification classifier is more accurate than the patient identification classifier, wherein the unknown patient identification prediction model is re-trained to generate the set of patient unknown identification prediction based on the updated patient identification classifier.

12. The method of any one of embodiments 1-11, wherein the third determination engine comprises a next best actions model, the method further comprising training the next best actions model to determine next best actions for ESRD patients comprising:

generating a next best actions classifier comprising:

determining, based on historical healthcare patient data, likelihood of patient hospitalization in patients due to fluid overload;

determining, based on the historical healthcare patient data, likelihood of patient missing hospital appointment;

determining, based on the historical healthcare patient data and a dialysis adequacy criterion, likelihood of patient having abnormal dialysis adequacy;

determining, based on the historical healthcare patient data, optimal dry weight in patients due to dialysis; and determining, based on the historical healthcare patient data, likelihood of patient ESA or IS dosages required to be altered, wherein the next best actions classifier comprises the likelihood of patient hospitalization in patients due to fluid overload, likelihood of patient missing hospital appointment, likelihood of patient having abnormal dialysis adequacy, optimal dry weight in patients due to dialysis, and likelihood of patient ESA or IS dosages required to be altered; and wherein the next best actions model is trained to generate the set of patient next best actions based on the next best actions classifier.

13. The method of embodiment 12, further comprising re-training the next best actions model, comprising:

receiving, by a computer system, updated historical patient data, the updated historical patient data comprising updated structured historical healthcare data and unstructured historical healthcare data;

generating an updated next best actions classifier comprising:

determining, based on updated historical healthcare patient data, likelihood of patient hospitalization in patients due to fluid overload;

determining, based on the updated historical healthcare patient data, likelihood of patient missing hospital appointment;

determining, based on the updated historical healthcare patient data and a dialysis adequacy criterion, likelihood of patient having abnormal dialysis adequacy;

determining, based on the updated historical healthcare patient data, optimal dry weight in patients due to dialysis;

determining, based on the updated historical healthcare patient data, likelihood of patient ESA or IS dosages required to be altered;

wherein the next best actions classifier comprises the likelihood of patient hospitalization in patients due to fluid overload, likelihood of patient missing hospital appointment, likelihood of patient having abnormal dialysis adequacy, optimal dry weight in patients due to dialysis, and likelihood of patient ESA or IS dosages required to be altered;

generating an accuracy score of the updated next best actions classifier and the next best actions classifier;

determining, based on comparing the accuracy score of the updated next best actions classifier with the accuracy score of the next best actions classifier, that the next best actions classifier is more accurate than the next best actions classifier; and overwriting the next best actions classifier with the updated next best actions classifier in response to determining that the updated next best actions classifier is more accurate than the next best actions classifier, wherein the next best actions model is re-trained to generate the set of patient next best actions based on the updated next best actions classifier.

14. A non-transitory computer readable storage medium comprising program instructions stored thereon that are executable by a processor to cause the method operations of any one of claims 1-13.

15. A system comprising:

a processor; and non-transitory computer readable storage medium comprising program instructions stored thereon that are executable by the processor to cause the method operations of any one of claims 1-13.

What is claimed is:

1. A method comprising:

receiving, by a computer system from a healthcare database, patient data, the patient data comprising structured healthcare data and unstructured healthcare data;

receiving, by a computer system, historical healthcare data, the historical healthcare data comprising:

historical structured healthcare data;

historical unstructured healthcare data; and labeled historical outcome data;

tuning one or more hyperparameters of a risk stratification model to increase predictive power and improve processing speed of the risk stratification model;

training, by the computer system, the risk stratification model using the historical healthcare data;

generating, by a first determination engine based on application of the patient data to the risk stratification model, a patient risk stratification, the generating of the patient risk stratification comprising:

generating stratification scoring of the patient based on the patient data, the stratification scoring comprising:

a stratification score for the patient that is indicative of the patient's susceptibility to developing a medical condition; and a binary classification for the patient that is indicative of a positive or negative treatment trend for the patient;

turning one or more hyperparameters of a risk level assignment model to increase predictive power and improve porcessing speed of the risk level assignment model;

training, by the computer system, the risk level assignment model using the historical healthcare data and associated stratification scores and binary classifications;

generating, by a second determination engine based on application of the patient data to the risk level assignment model, a patient risk level assignment, the generating of the patient risk level assignment comprising:
generating risk level scoring of the patient; and
determining, based on the risk level scoring of the patient, a risk category for the patient;
tuning one or more hyperparameters of a next best actions model to increase predictive power and improve processing speed of the next best actions model;
training, by the computer system, the next best action model using labeled historical outcome data of the historical healthcare data and associated stratification scores, binary classifications, and risk categories for the patients;
generating, by a third determination engine based on application of the patient data and the stratification score, binary classification, and risk category for the patient, a set of patient next best actions, the generating of the set of patient next best actions comprising:
determining, based on the patient data, a patient outcome prediction; and
generating, based on the patient outcome prediction, the set of patient next best actions;
generating, by a fourth determination engine, a patient disease state transition prediction, the generating of the patient disease state transition prediction comprising:
determining, based on application of the patient data to a disease state transition prediction model, a set of transition probabilities for the patient;
generating, by a fifth determination engine, a patient unknown identification prediction, the generating of the patient unknown identification prediction comprising:
determining, based on application of the patient data to an unknown patient identification prediction model, a disease propensity score for the patient; and
generating, by a sixth determination engine based on the patient risk stratification, patient risk level assignment, patient next best actions, patient disease state transition predictions, and patient unknown identification predictions, a patient diagnosis report comprising a treatment action,
the treatment action for use in treating a patient.

2. The method of claim 1, wherein the first determination engine comprises the risk stratification model, and the training of the risk stratification model, comprising:
generating a binary risk classifier comprising determining, based on the historical patient healthcare data, key risk features and thresholds, wherein the binary risk classifier comprises the key risk features and thresholds, and
wherein the risk stratification model is trained to generate the patient risk stratification based on the binary risk classifier.

3. The method of claim 2, further comprising re-training the risk stratification model, comprising:
receiving, by a computer system, updated historical patient data, the updated historical patient data comprising updated structured historical healthcare data and unstructured historical healthcare data;
generating an updated binary risk classifier comprising determining, based on the updated historical patient healthcare data, key risk features and thresholds, wherein the binary risk classifier comprises the key risk features and thresholds;
generating an accuracy score of the updated binary risk classifier and the binary risk classifier;
determining, based on comparing the accuracy score of the updated binary risk classifier with the accuracy score of the binary risk classifier, that the updated risk classifier is more accurate than the binary risk classifier; and
overwriting the binary risk classifier with the updated risk classifier in response to determining that the updated binary risk classifier is more accurate than the binary risk classifier,
wherein the risk stratification model is re-trained to generate the patient risk stratification based on the updated binary risk classifier.

4. The method of claim 1, wherein the second determination engine comprises the risk level assignment model, and the training of the risk level assignment model, comprising:
generating a multi-class risk level classifier comprising determining, based on the historical healthcare patient data and the binary classification of the patient, key risk features, wherein the multi-class risk level classifier comprises the key risk features; and
wherein the risk level assignment model is trained to generate the patient risk level assignment based on the multi-class risk level classifier.

5. The method of claim 4, further comprising re-training the risk level assignment model, comprising:
receiving, by a computer system, updated historical patient data, the updated historical patient data comprising updated structured historical healthcare data and unstructured historical healthcare data;
generating an updated multi-class risk level classifier comprising determining, based on the updated historical patient healthcare data and the binary classification of the patient, key risk features, wherein the multi-class risk level classifier comprises the key risk features;
generating an accuracy score of the updated multi-class risk level classifier and the multi-class risk level classifier;
determining, based on comparing the accuracy score of the updated multi-class risk level classifier with the accuracy score of the multi-class risk level classifier, that the updated multi-class risk level classifier is more accurate than the multi-class risk level risk classifier; and
overwriting the multi-class risk level classifier with the updated multi-class risk level classifier in response to determining that the updated multi-class risk level classifier is more accurate than the multi-class risk level risk classifier,
wherein the risk level assignment model is re-trained to generate the patient risk level assignment based on the updated multi-class risk level classifier.

6. The method of claim 1, wherein the third determination engine comprises the next best actions model, and the training of the next best actions model, comprising:
generating a next best actions classifier comprising determining, based on the historical healthcare patient data, key risk features and thresholds, wherein the next best actions classifier comprises the key risk features and thresholds; and
wherein the next best actions model is trained to generate the set of patient next best actions based on the next best actions classifier.

7. The method of claim 6, further comprising re-training the next best actions model, comprising:
receiving, by a computer system, updated historical patient data, the updated historical patient data comprising updated structured historical healthcare data and unstructured historical healthcare data;

generating an updated next best actions classifier comprising determining, based on the updated historical patient healthcare data, key risk features and thresholds, wherein the next best actions classifier comprises the key risk features and thresholds;

generating an accuracy score of the updated next best actions classifier and the next best actions classifier;

determining, based on comparing the accuracy score of the updated next best actions classifier with the accuracy score of the next best actions classifier, that the next best actions classifier is more accurate than the next best actions classifier; and overwriting the next best actions classifier with the updated next best actions classifier in response to determining that the updated next best actions classifier is more accurate than the next best actions classifier, wherein the next best actions model is re-trained to generate the set of patient next best actions based on the updated next best actions classifier.

8. The method of claim 1, wherein the fourth determination engine comprises the disease state transition prediction model, and the method further comprising training the disease state transition prediction model, comprising:

generating a disease state transition classifier comprising determining, based on the historical healthcare patient data, key disease state features and thresholds, wherein the disease state transition classifier comprises the key disease state features and thresholds; and wherein the disease state transition prediction model is trained to generate the patient disease state transition prediction based on the disease state transition classifier.

9. The method of claim 8, further comprising re-training the disease state transition prediction model, comprising:

receiving, by a computer system, updated historical patient data, the updated historical patient data comprising updated structured historical healthcare data and unstructured historical healthcare data;

generating an updated disease state transition classifier comprising determining, based on the updated historical patient healthcare data, key disease state features and thresholds, wherein the disease state transition classifier comprises the key disease state features and thresholds;

generating an accuracy score of the updated disease state transition classifier and the disease state transition classifier;

determining, based on comparing the accuracy score of the updated disease state transition classifier with the accuracy score of the disease state transition classifier, that the disease state transition classifier is more accurate than the disease state transition classifier; and overwriting the disease state transition classifier with the updated disease state transition classifier in response to determining that the updated disease state transition classifier is more accurate than the disease state transition classifier, wherein the disease state transition prediction model is re-trained to the patient disease state transition prediction based on the updated disease state transition classifier.

10. The method of claim 1, wherein the fifth determination engine comprises the unknown patient identification prediction model, and the method further comprising training the unknown patient identification prediction model, comprising:

generating a patient identification classifier comprising determining, based on the historical healthcare patient data, key patient features and thresholds, wherein the patient identification classifier comprises the key patient features and thresholds; and wherein the unknown patient identification prediction model is trained to generate the patient unknown identification prediction based on the patient identification classifier.

11. The method of claim 10, further comprising re-training the unknown patient identification prediction model, comprising:

receiving, by a computer system, updated historical patient data, the updated historical patient data comprising updated structured historical healthcare data and unstructured historical healthcare data;

generating an updated patient identification classifier comprising determining, based on the updated historical patient healthcare data, key patient features and thresholds, wherein the patient identification classifier comprises the key patient features and thresholds;

generating an accuracy score of the updated patient identification classifier and the patient identification classifier;

determining, based on comparing the accuracy score of the updated a-patient identification classifier with the accuracy score of the patient identification classifier, that the patient identification classifier is more accurate than the patient identification classifier; and overwriting the patient identification classifier with the updated patient identification classifier in response to determining that the updated patient identification classifier is more accurate than the patient identification classifier, wherein the unknown patient identification prediction model is re-trained to generate the set of patient unknown identification prediction based on the updated patient identification classifier.

12. The method of claim 1, the method further comprising training the next best actions model to determine next best actions for ESRD patients comprising:

generating a next best actions classifier comprising:

determining, based on historical healthcare patient data, likelihood of patient hospitalization in patients due to fluid overload;

determining, based on the historical healthcare patient data, likelihood of patient missing hospital appointment;

determining, based on the historical healthcare patient data and a dialysis adequacy criterion, likelihood of patient having abnormal dialysis adequacy;

determining, based on the historical healthcare patient data, optimal dry weight in patients due to dialysis; and determining, based on the historical healthcare patient data, likelihood of patient ESA or IS dosages required to be altered, wherein the next best actions classifier comprises the likelihood of patient hospitalization in patients due to fluid overload, likelihood of patient missing hospital appointment, likelihood of patient having abnormal dialysis adequacy, optimal dry weight in patients due to dialysis, and likelihood of patient ESA or IS dosages required to be altered; and wherein the next best actions model is trained to generate the set of patient next best actions based on the next best actions classifier.

13. The method of claim 12, further comprising re-training the next best actions model, comprising:

receiving, by a computer system, updated historical patient data, the updated historical patient data comprising updated structured historical healthcare data and unstructured historical healthcare data;

generating an updated next best actions classifier comprising:

determining, based on updated historical healthcare patient data, likelihood of patient hospitalization in patients due to fluid overload;

determining, based on the updated historical healthcare patient data, likelihood of patient missing hospital appointment;

determining, based on the updated historical healthcare patient data and a dialysis adequacy criterion, likelihood of patient having abnormal dialysis adequacy;

determining, based on the updated historical healthcare patient data, optimal dry weight in patients due to dialysis;

determining, based on the updated historical healthcare patient data, likelihood of patient ESA or IS dosages required to be altered;

wherein the next best actions classifier comprises the likelihood of patient hospitalization in patients due to fluid overload, likelihood of patient missing hospital appointment, likelihood of patient having abnormal dialysis adequacy, optimal dry weight in patients due to dialysis, and likelihood of patient ESA or IS dosages required to be altered;

generating an accuracy score of the updated next best actions classifier and the next best actions classifier;

determining, based on comparing the accuracy score of the updated next best actions classifier with the accuracy score of the next best actions classifier, that the next best actions classifier is more accurate than the next best actions classifier; and overwriting the next best actions classifier with the updated next best actions classifier in response to determining that the updated next best actions classifier is more accurate than the next best actions classifier, wherein the next best actions model is re-trained to generate the set of patient next best actions based on the updated next best actions classifier.

14. A non-transitory computer readable storage medium comprising program instructions stored thereon that are executable by a processor to cause the following operations:

receiving, by a computer system from a healthcare database, patient data, the patient data comprising structured healthcare data and unstructured healthcare data;

receiving, by a computer system, historical healthcare data, the historical healthcare data comprising:

historical structured healthcare data;

historical unstructured healthcare data; and labeled historical outcome data;

tuning one or more hyperparameters of a risk stratication model to increase predictive power and improve processing speed of the risk stratification model;

training, by the computer system, the risk stratification model using the historical healthcare data;

generating, by a first determination engine based on application of the patient data to the risk stratification model, a patient risk stratification, the generating of the patient risk stratification comprising:

generating stratification scoring of the patient based on the patient data, the stratification scoring comprising:

a stratification score for the patient that is indicative of the patient's susceptibility to developing a medical condition; and a binary classification for the patient that is indicative of a positive or negative treatment trend for the patient;

tuning one or more hyperarameters of a risk level assignment model to increase predictive power and improve processing spped of the risk level assignment model;

training, by the computer system, the risk level assignment model using the historical healthcare data and associated stratification scores and binary classifications;

generating, by a second determination engine based on application of the patient data to the risk level assignment model, a patient risk level assignment, the generating of the patient risk level assignment comprising:

generating risk level scoring of the patient; and determining, based on the risk level scoring of the patient, a risk category for the patient;

tuning one or more hyperparameters of a next best actions model to incrase predictive power and improve processing speed of the next best actions model;

training, by the computer system, the next best actions model using labeled historical outcome data of the historical healthcare data and associated stratification scores, binary classifications, and risk categories for the patients;

generating, by a third determination engine based on application of the patient data and the stratification score, binary classification, and risk category for the patient, a set of patient next best actions, the generating of the set of patient next best actions comprising:

determining, based on the patient data, a patient outcome prediction; and generating, based on the patient outcomes prediction, the set of patient next best actions;

generating, by a fourth determination engine, a patient disease state transition prediction, the generating of the patient disease state transition prediction comprising:

determining, based on application of the patient data to a disease state transition prediction model, a set of transition probabilities for the patient;

generating, by a fifth determination engine, a patient unknown identification prediction, the generating of the patient unknown identification prediction comprising:

determining, based on application of the patient data to an unknown patient identification prediction model, a disease propensity score for the patient; and generating, by a sixth determination engine based on the patient risk stratification, patent risk level assignment, patient next best actions, patient disease state transition predictions, and patient unknown identification predictions, a patient diagnosis report comprising a treatment action, the treatment action for use in treating a patient.

15. A system comprising:

a processor; and non-transitory computer readable storage medium comprising program instructions stored thereon that are executable by the processor to cause the following operations:

receiving, by a computer system from a healthcare database, patient data, the patient data comprising structured healthcare data and unstructured healthcare data;

receiving, by a computer system, historical healthcare data, the historical healthcare data comprising:
historical structured healthcare data;
historical unstructured healthcare data; and
labeled historical outcome data;

tuning one or more hyperparameters of a risk stratification model to increase predictive power and improve processing speed of the risk stratification model;

training, by the computer system, the risk stratification model using the historical healthcare data;

generating, by a first determination engine based on application of the patient data to the risk stratification model, a patient risk stratification, the generating of the patient risk stratification comprising:
generating stratification scoring of the patient based on the patient data, the stratification scoring comprising:
a stratification score for the patient that is indicative of the patient's susceptibility to developing a medical condition; and
a binary classification for the patient that is indicative of a positive or negative treatment trend for the patient;

tuning one or more hyperparameters of a risk level assignment model to increase predictive power and improve processing speed of the risk level assignment model;

training, by the computer system, the risk level assignment model using the historical healthcare data and associated stratification scores and binary classifications;

generating, by a second determination engine based on application of the patient data to the risk level assignment model, a patient risk level assignment, the generating of the patient risk level assignment comprising:
generating risk level scoring of the patient; and
determining, based on the risk level scoring of the patient, a risk category for the patient;

tuning one or more hyperparameters of a next best actions model to increase predictive power and improve processing speed of the next best actions model;

training, by the computer system, the next best actions model using labeled historical outcome data of the historical healthcare data and associated stratification scores, binary classifications, and risk categories for the patients;

generating, by a third determination engine based on application of the patient data and the stratification score, binary classification, and risk category for the patient, a set of patient next best actions, the generating of the set of patient next best actions comprising:

determining, based on the patient data, a patient outcome prediction; and generating, based on the predictions of patient outcomes prediction, the set of patient next best actions;

generating, by a fourth determination engine, a patient disease state transition prediction, the generating of the patient disease state transition prediction comprising:

determining, based on application of the patient data to a disease state transition prediction model, a set of transition probabilities for the patient;

generating, by a fifth determination engine, a patient unknown identification prediction, the generating of the patient unknown identification prediction comprising:

determining, based on application of the patient data to an unknown patient identification prediction model, a disease propensity score for the patient; and generating, by a sixth determination engine based on the patient risk stratification, patent risk level assignment, patient next best actions, patient disease state transition predictions, and patient unknown identification predictions, a patient diagnosis report comprising a treatment action, the treatment action for use in treating a patient.

* * * * *